(12) United States Patent
Muse

(10) Patent No.: US 10,980,522 B2
(45) Date of Patent: Apr. 20, 2021

(54) INTRAOSSEOUS ACCESS DEVICES, SYSTEMS, AND METHODS

(71) Applicant: Piper Access, LLC, Salt Lake City, UT (US)

(72) Inventor: Jay Muse, Salt Lake City, UT (US)

(73) Assignee: Piper Access, LLC, Salt Lake City, UT (US)

( * ) Notice: Subject to any disclaimer, the term of this patent is extended or adjusted under 35 U.S.C. 154(b) by 217 days.

(21) Appl. No.: 15/787,671

(22) Filed: Oct. 18, 2017

(65) Prior Publication Data

US 2018/0125465 A1     May 10, 2018

Related U.S. Application Data

(60) Provisional application No. 62/409,825, filed on Oct. 18, 2016, provisional application No. 62/600,857, (Continued)

(51) Int. Cl.
*A61B 10/02*     (2006.01)
*A61B 17/16*     (2006.01)
(Continued)

(52) U.S. Cl.
CPC ........ *A61B 10/025* (2013.01); *A61B 17/1637* (2013.01); *A61B 17/3472* (2013.01);
(Continued)

(58) Field of Classification Search
CPC .............. A61B 10/025; A61B 17/1637; A61B 17/32002; A61B 17/3472; A61M 2210/02
See application file for complete search history.

(56) References Cited

U.S. PATENT DOCUMENTS 1,436,707 A    11/1922   Gaschke
2,317,648 A     4/1943   Siqveland
(Continued)

FOREIGN PATENT DOCUMENTS

CA        2207561      6/1997
DE    102007005963 A1   8/2008
(Continued)

OTHER PUBLICATIONS

Patent Cooperation Treaty International Searching Authority, Notification of Transmittal of the International Search Report and the Written Opinion of the International Searching Authority for International Application No. PCT/US17/57270, dated Jan. 12, 2018, 12 pages.
(Continued)

*Primary Examiner* — Christine H Matthews
(74) *Attorney, Agent, or Firm* — Med Venture Management, LLC; Daniel C. Higgs

(57) ABSTRACT

An intraosseous access system can include a needle that defines a lumen and a longitudinal axis about which the needle can be rotated during an insertion event. The needle can include a proximal end that remains at an exterior of a patient during use, a distal end that can be inserted through the skin of the patient into contact with a bone of the patient, and a distal tip at a distalmost point of the distal end of the needle that is positioned at the longitudinal axis of the needle. The system can further include an obturator sized to be received within the lumen of the needle that can inhibit material from entering the needle as the system is inserted into the bone.

19 Claims, 15 Drawing Sheets

Related U.S. Application Data filed on Mar. 7, 2017, provisional application No. 62/525,663, filed on Jun. 27, 2017.

(51) Int. Cl.
  *A61B 17/34* (2006.01)
  *A61M 5/158* (2006.01)
  *A61B 17/32* (2006.01)

(52) U.S. Cl.
  CPC ......... *A61M 5/158* (2013.01); *A61B 10/0283* (2013.01); *A61B 17/32002* (2013.01); *A61M 2210/02* (2013.01)

(56) References Cited

U.S. PATENT DOCUMENTS

| | | |
|---|---|---|
| 4,275,721 A | 6/1981 | Olson |
| 4,321,914 A | 3/1982 | Begovac et al. |
| 4,356,828 A | 11/1982 | Jamshidi |
| 4,469,109 A | 9/1984 | Mehl |
| 4,593,681 A | 6/1986 | Soni |
| 4,755,170 A | 7/1988 | Golden |
| 4,755,173 A | 7/1988 | Konopka et al. |
| 4,758,225 A | 7/1988 | Cox et al. |
| 4,889,529 A | 12/1989 | Haindl |
| 4,929,241 A | 5/1990 | Kulli |
| 4,944,677 A | 7/1990 | Alexandre |
| 4,952,207 A | 8/1990 | Lemieux |
| 4,964,854 A | 10/1990 | Luther |
| 4,969,870 A | 11/1990 | Kramer et al. |
| 4,978,344 A | 12/1990 | Dombrowski et al. |
| 5,040,542 A | 8/1991 | Gray |
| 5,042,558 A | 8/1991 | Hussey et al. |
| 5,049,136 A | 9/1991 | Johnson |
| 5,053,017 A | 10/1991 | Chamuel |
| 5,073,169 A | 12/1991 | Raiken |
| 5,120,321 A | 6/1992 | Oksman et al. |
| 5,122,114 A | 6/1992 | Miller et al. |
| 5,135,504 A | 8/1992 | McLees |
| 5,137,520 A | 8/1992 | Maxson et al. |
| 5,183,468 A | 2/1993 | McLees |
| 5,207,697 A | 5/1993 | Carusillo et al. |
| 5,215,528 A | 6/1993 | Purdy et al. |
| 5,263,939 A | 11/1993 | Wortrich |
| 5,271,744 A | 12/1993 | Kramer et al. |
| 5,279,591 A | 1/1994 | Simon |
| 5,300,045 A | 4/1994 | Plassche, Jr. |
| 5,304,151 A | 4/1994 | Kuracina |
| 5,312,351 A | 5/1994 | Gerrone |
| 5,312,364 A | 5/1994 | Jacobs |
| 5,322,517 A | 6/1994 | Sircom et al. |
| 5,328,482 A | 7/1994 | Sircom et al. |
| 5,332,398 A | 7/1994 | Miller et al. |
| 5,334,158 A | 8/1994 | McLees |
| 5,344,408 A | 9/1994 | Partika |
| 5,348,544 A | 9/1994 | Sweeney et al. |
| 5,354,283 A | 10/1994 | Bark et al. |
| 5,357,974 A * | 10/1994 | Baldridge ............ A61B 10/025 600/567 |
| 5,364,367 A | 11/1994 | Banks et al. |
| 5,366,446 A | 11/1994 | Tal et al. |
| 5,368,046 A | 11/1994 | Scarfone et al. |
| 5,375,588 A | 12/1994 | Yoon |
| 5,405,348 A | 4/1995 | Anspach, Jr. et al. |
| 5,423,766 A | 6/1995 | Di Cesare |
| 5,431,655 A | 7/1995 | Melker et al. |
| 5,449,370 A | 9/1995 | Vaitekunas |
| 5,451,210 A | 9/1995 | Kramer et al. |
| 5,458,658 A | 10/1995 | Sircom |
| 5,472,427 A | 12/1995 | Rammler |
| 5,533,974 A | 7/1996 | Gaba |
| 5,554,154 A | 9/1996 | Rosenberg |
| 5,556,411 A | 9/1996 | Taoda et al. |
| 5,558,651 A | 9/1996 | Crawford et al. |
| 5,562,633 A | 10/1996 | Wozencroft |
| 5,571,133 A | 11/1996 | Yoon |
| 5,584,810 A | 12/1996 | Brimhall |
| 5,591,188 A | 1/1997 | Waisman |
| 5,601,559 A | 2/1997 | Melker et al. |
| 5,662,610 A | 9/1997 | Sircom |
| 5,683,378 A | 11/1997 | Christy |
| 5,697,907 A | 12/1997 | Gaba |
| 5,779,708 A | 7/1998 | Wu |
| 5,807,275 A | 9/1998 | Jamshidi |
| 5,882,337 A | 3/1999 | Bogert et al. |
| 6,001,080 A | 12/1999 | Kuracina et al. |
| 6,004,294 A | 12/1999 | Brimhall et al. |
| 6,071,284 A | 6/2000 | Fox |
| 6,077,244 A | 6/2000 | Botich et al. |
| 6,117,108 A | 9/2000 | Woehr et al. |
| 6,132,401 A | 10/2000 | Van Der Meyden et al. |
| 6,135,769 A | 10/2000 | Kwan |
| 6,183,442 B1 | 2/2001 | Athanasiou et al. |
| 6,228,088 B1 | 5/2001 | Miller et al. |
| 6,247,928 B1 | 6/2001 | Meller et al. |
| 6,273,715 B1 | 8/2001 | Meller et al. |
| 6,287,278 B1 | 9/2001 | Woehr et al. |
| 6,443,927 B1 | 9/2002 | Cook |
| 6,443,929 B1 | 9/2002 | Kuracina et al. |
| 6,585,704 B2 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,626,887 B1 | 9/2003 | Wu |
| 6,629,959 B2 | 10/2003 | Kuracina et al. |
| 6,652,486 B2 | 11/2003 | Bialecki et al. |
| 6,652,490 B2 | 11/2003 | Howell |
| 6,699,242 B2 | 3/2004 | Heggeness |
| 6,749,588 B1 | 6/2004 | Howell et al. |
| 6,761,726 B1 | 7/2004 | Findlay et al. |
| 6,796,962 B2 | 9/2004 | Ferguson et al. |
| 6,814,734 B2 | 11/2004 | Chappuis et al. |
| 6,860,871 B2 | 3/2005 | Kuracina et al. |
| 6,875,219 B2 | 4/2005 | Arramon et al. |
| 6,902,546 B2 | 6/2005 | Ferguson |
| 6,984,213 B2 | 1/2006 | Horner et al. |
| 7,004,927 B2 | 2/2006 | Ferguson et al. |
| 7,008,402 B2 | 3/2006 | Ferguson et al. |
| 7,070,580 B2 | 7/2006 | Nielsen |
| 7,179,244 B2 | 2/2007 | Smith et al. |
| 7,226,434 B2 | 6/2007 | Carlyon et al. |
| 7,264,613 B2 | 9/2007 | Woehr et al. |
| 7,341,573 B2 | 3/2008 | Ferguson et al. |
| 7,354,422 B2 | 4/2008 | Riesenberger et al. |
| 7,357,784 B2 | 4/2008 | Ferguson |
| 7,413,562 B2 | 8/2008 | Ferguson et al. |
| 7,458,954 B2 | 12/2008 | Ferguson et al. |
| 7,524,306 B2 | 4/2009 | Botich et al. |
| 7,588,559 B2 | 9/2009 | Aravena et al. |
| 7,601,139 B2 | 10/2009 | Woehr et al. |
| 7,611,485 B2 | 11/2009 | Ferguson |
| 7,618,395 B2 | 11/2009 | Ferguson |
| 7,670,328 B2 | 3/2010 | Miller |
| 7,699,808 B2 | 4/2010 | Marrs et al. |
| 7,699,850 B2 | 4/2010 | Miller |
| 7,749,225 B2 | 7/2010 | Chappuis et al. |
| 7,811,260 B2 | 10/2010 | Miller et al. |
| 7,815,642 B2 | 10/2010 | Miller |
| 7,850,620 B2 | 12/2010 | Miller et al. |
| 7,935,080 B2 | 5/2011 | Howell et al. |
| 7,967,792 B2 | 6/2011 | Bierman |
| 7,972,339 B2 | 7/2011 | Nassiri et al. |
| 8,038,664 B2 | 10/2011 | Miller et al. |
| 8,043,229 B2 | 10/2011 | Mulvihill et al. |
| 8,096,973 B2 | 1/2012 | Snow et al. |
| 8,142,365 B2 | 3/2012 | Miller |
| 8,206,355 B2 | 6/2012 | Thorne |
| 8,211,070 B2 | 7/2012 | Woehr et al. |
| 8,246,584 B2 | 8/2012 | Aravena et al. |
| 8,486,024 B2 | 7/2013 | Steube |
| 8,506,568 B2 | 8/2013 | Miller |
| 8,591,467 B2 | 11/2013 | Walker et al. |
| 8,628,497 B2 | 1/2014 | Finnestad et al. |
| 8,641,715 B2 | 2/2014 | Miller |

(56) References Cited

U.S. PATENT DOCUMENTS

| | | |
|---|---|---|
| 8,656,929 B2 | 2/2014 | Miller et al. |
| 8,668,698 B2 | 3/2014 | Miller et al. |
| 8,684,978 B2 | 4/2014 | Miller et al. |
| 8,715,287 B2 | 5/2014 | Miller |
| 8,844,112 B2 | 9/2014 | Snow et al. |
| 8,845,584 B2 | 9/2014 | Ferguson et al. |
| 8,864,714 B2 | 10/2014 | Harding et al. |
| 8,876,826 B2 | 11/2014 | Miller |
| 8,926,563 B2 | 1/2015 | Steube |
| 8,944,069 B2 | 2/2015 | Miller et al. |
| 8,974,410 B2 | 3/2015 | Miller et al. |
| 8,992,535 B2 | 3/2015 | Miller |
| 9,072,543 B2 | 7/2015 | Miller et al. |
| 9,220,483 B2 | 12/2015 | Frankhouser et al. |
| 9,295,487 B2 | 3/2016 | Miller et al. |
| 9,314,228 B2 | 4/2016 | Miller |
| 9,314,270 B2 | 4/2016 | Miller |
| 9,393,031 B2 | 7/2016 | Miller |
| 9,399,119 B2 | 7/2016 | Kuracina et al. |
| 9,408,632 B2 | 8/2016 | Erskine |
| 9,414,815 B2 | 8/2016 | Miller et al. |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,539,398 B2 | 1/2017 | Ferguson et al. |
| 9,545,243 B2 | 1/2017 | Miller et al. |
| 9,889,255 B2 | 2/2018 | Sonderegger et al. |
| 2001/0011164 A1 | 8/2001 | Bierman |
| 2002/0123724 A1 | 9/2002 | Douglas et al. |
| 2003/0225411 A1 | 12/2003 | Miller |
| 2004/0220497 A1 | 11/2004 | Findlay et al. |
| 2005/0027263 A1 | 2/2005 | Woehr et al. |
| 2005/0033235 A1 | 2/2005 | Flint |
| 2005/0101933 A1 | 5/2005 | Marrs et al. |
| 2005/0107743 A1 | 5/2005 | Fangrow, Jr. |
| 2005/0165404 A1 | 7/2005 | Miller |
| 2005/0245878 A1 | 11/2005 | Mernoe et al. |
| 2006/0015066 A1 | 1/2006 | Turieo et al. |
| 2006/0025723 A1 | 2/2006 | Ballarini |
| 2006/0106402 A1 | 5/2006 | McLucas |
| 2007/0049945 A1 | 3/2007 | Miller |
| 2007/0270775 A1 | 11/2007 | Miller et al. |
| 2008/0140014 A1 | 6/2008 | Miller et al. |
| 2008/0215056 A1 | 9/2008 | Miller et al. |
| 2008/0221580 A1 | 9/2008 | Miller et al. |
| 2009/0054808 A1 | 2/2009 | Miller |
| 2009/0093830 A1 | 4/2009 | Miller |
| 2009/0204024 A1 | 8/2009 | Miller |
| 2009/0306697 A1 | 12/2009 | Fischvogt |
| 2010/0152616 A1 | 6/2010 | Beyhan et al. |
| 2011/0028976 A1 | 2/2011 | Miller |
| 2011/0082387 A1 | 4/2011 | Miller et al. |
| 2013/0030370 A1 | 1/2013 | Walker et al. |
| 2013/0096561 A1 | 4/2013 | Miller et al. |
| 2014/0100528 A1 | 4/2014 | Finnestad et al. |
| 2014/0142577 A1 | 5/2014 | Miller |
| 2014/0276471 A1 | 9/2014 | Emery et al. |
| 2014/0277028 A1 | 9/2014 | Voic |
| 2014/0343454 A1 | 11/2014 | Miller et al. |
| 2015/0127006 A1 | 5/2015 | Miller |
| 2015/0230823 A1 | 8/2015 | Morgan et al. |
| 2015/0231364 A1 | 8/2015 | Blanchard et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0183974 A1 | 6/2016 | Miller |
| 2016/0184509 A1 | 6/2016 | Miller et al. |
| 2016/0206346 A1 | 7/2016 | Miller |
| 2017/0007271 A1 | 1/2017 | Miller et al. |
| 2018/0125465 A1 | 5/2018 | Muse et al. |
| 2018/0256209 A1 | 9/2018 | Muse et al. |
| 2018/0256870 A1 | 9/2018 | Muse et al. |

FOREIGN PATENT DOCUMENTS

| | | |
|---|---|---|
| EP | 0548612 A1 | 6/1993 |
| EP | 2849656 B1 | 5/2013 |
| EP | 2967508 B1 | 1/2016 |
| FR | 2481930 | 11/1981 |
| FR | 2522973 A2 | 9/1983 |
| FR | 2885512 A1 | 11/2006 |
| JP | 2000140125 A | 12/1998 |
| NL | 9401085 A | 6/1994 |
| WO | 200213893 A1 | 2/2002 |
| WO | 2008065646 A1 | 6/2008 |
| WO | 2013173360 A1 | 11/2013 |
| WO | 2014144239 A1 | 9/2014 |
| WO | 2018075694 A1 | 4/2018 |

OTHER PUBLICATIONS

Promethus Medical Ltd., Prometheus PIN, Undated, Downloaded from https://www.prometheusmedical.co.uk/equipment/prometheus-equipment-intraosseous-access/prometheus-pin on Aug. 10, 2017.

United States Patent and Trademark Office, Office Action in U.S. Appl. No. 15/914,964, dated Aug. 21, 2020, 19 pages.

United States Patent and Trademark Office, Office Action in U.S. Appl. No. 15/915,606, dated Sep. 23, 2020, 10 pages.

U.S. Appl. No. 15/787,671, filed Oct. 18, 2017, Intraosseous Access Devices, Systems, and Methods.

U.S. Appl. No. 15/914,964, filed Mar. 7, 2018, Safety Shields for Elongated Instruments and Related Systems and Methods.

U.S. Appl. No. 15/915,606 filed Mar. 8, 2018, Securement Devices, Systems, and Methods.

* cited by examiner

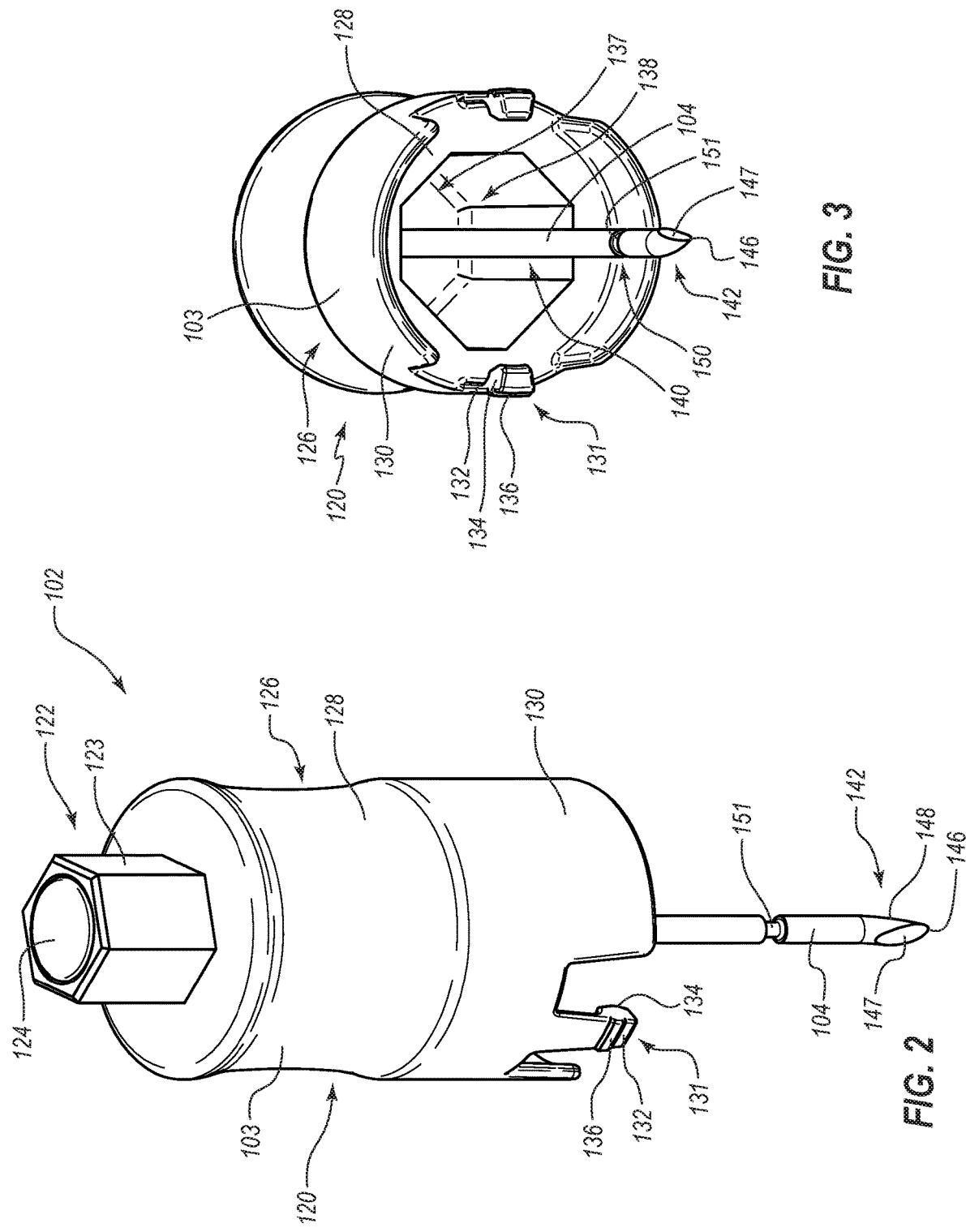

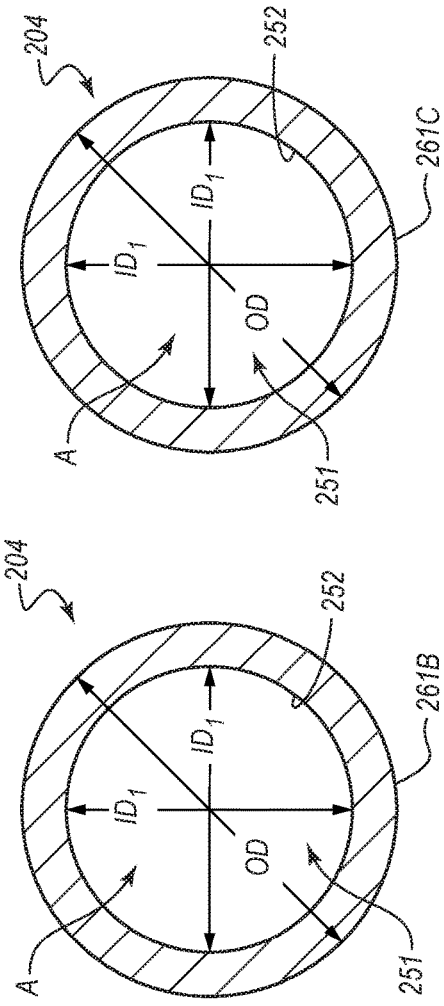
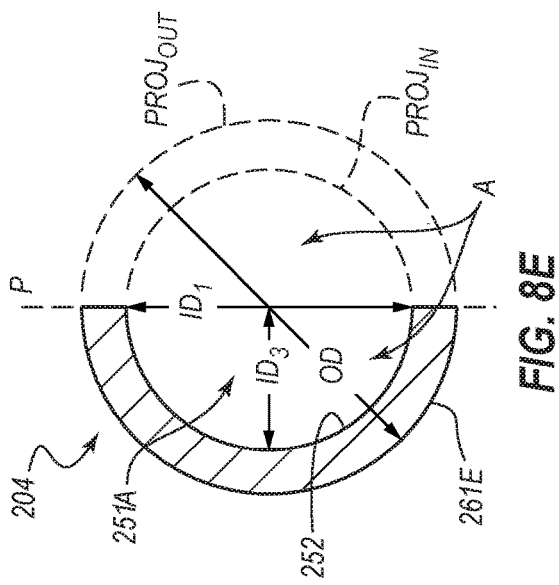
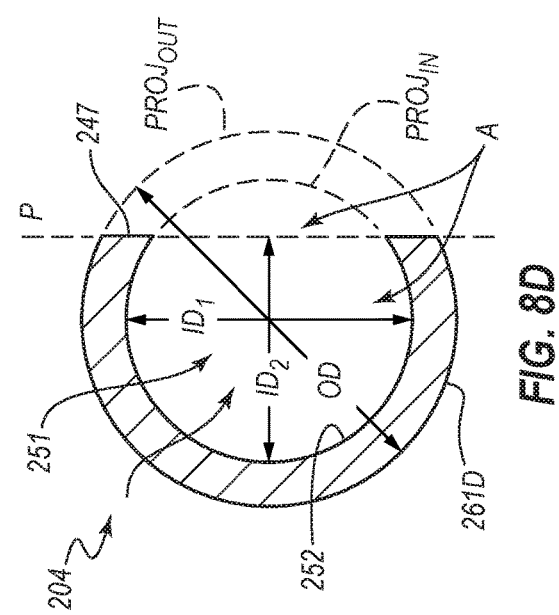

INTRAOSSEOUS ACCESS DEVICES, SYSTEMS, AND METHODS

CROSS-REFERENCE TO RELATED APPLICATIONS

This application claims the benefit under 35 U.S.C. § 119(e) of U.S. Provisional Patent Application No. 62/409,825, titled INTRAOSSEOUS ACCESS DEVICES, SYSTEMS, AND METHODS, filed on Oct. 18, 2016; U.S. Provisional Patent Application No. 62/600,857, titled NEEDLE TIP CAPTURE MECHANISM, filed on Mar. 7, 2017; and U.S. Provisional Patent Application No. 62/525,663, titled SAFETY SHIELDS FOR ELONGATED INSTRUMENTS AND RELATED SYSTEMS AND METHODS, filed on Jun. 27, 2017, the entire contents of each of which are hereby incorporated by reference herein.

TECHNICAL FIELD

Certain embodiments described herein relate generally to devices, systems, and methods for accessing an interior of a bone of a patient, and further embodiments relate more particularly to devices, systems, and methods for achieving intraosseous access, such as for intraosseous infusion.

BACKGROUND

Many devices, systems, and methods have been developed to for accessing an interior of a bone of a patient, including for such purposes as intraosseous access. Known devices, systems, and methods, however, suffer from one or more drawbacks that can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2 is a perspective view of an embodiment of an obturator assembly portion of the intraosseous access system of FIG. 1;

FIG. 3 is a further perspective view of the obturator assembly;

FIGS. 8A-8E are cross-sectional views of the needle taken along the view lines 8A-8A, 8B-8B, 8C-8C, 8D-8D, and 8E-8E, respectively, in FIG. 7;

DETAILED DESCRIPTION

Figure 1:
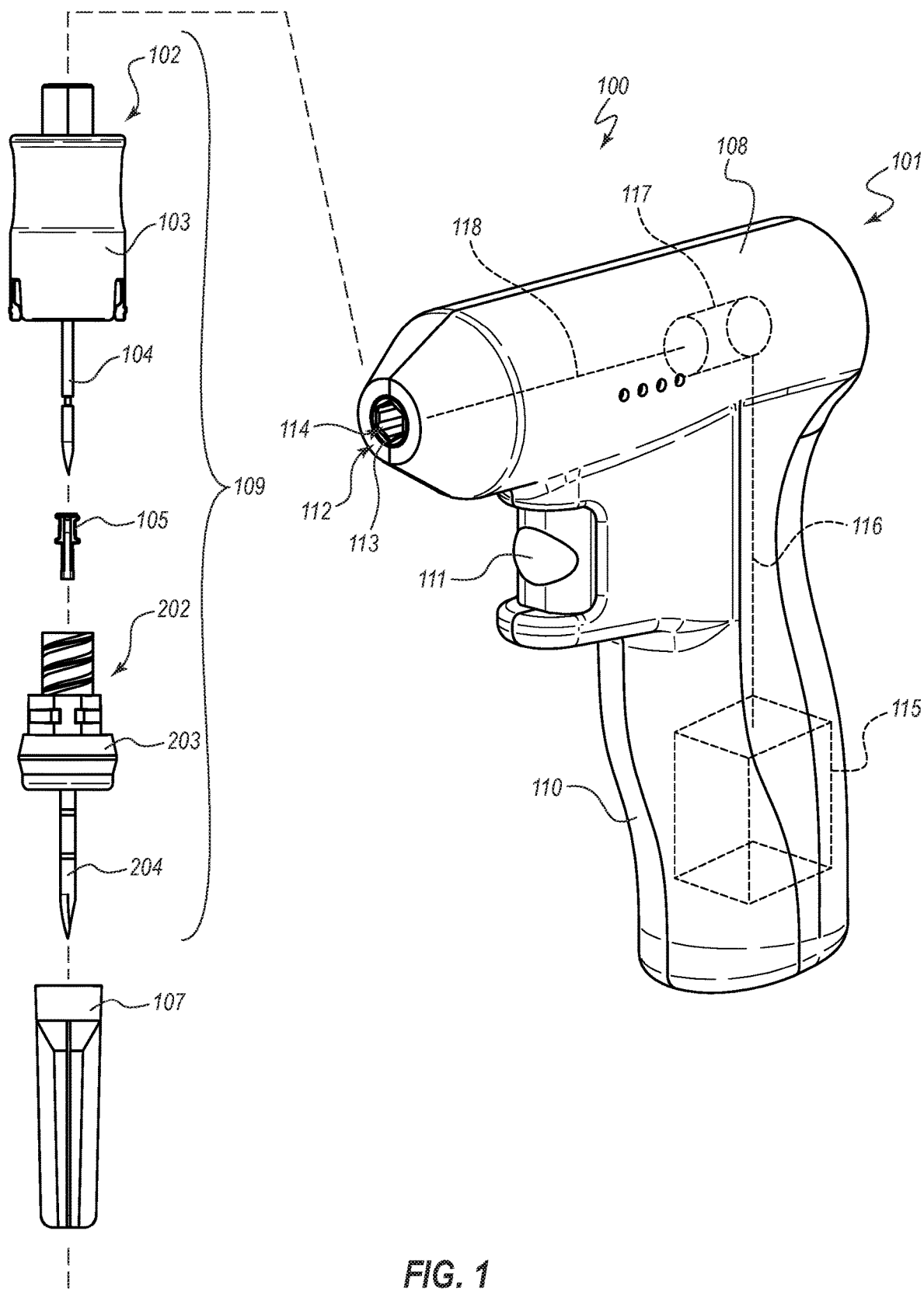
FIG. 1 is an exploded view of an embodiment of an intraosseous access system, wherein an access assembly subset of the system is depicted slightly enlarged and in elevation, and an automated driver component is depicted in perspective.

The present disclosure relates generally to bone penetrating devices, systems, and methods. In particular, certain embodiments disclosed herein can be used for drilling through or otherwise being inserted into or penetrating hard, compact bone tissue (cortical bone) to gain access to soft bone tissue (cancellous bone) or bone marrow. For example, certain embodiments are particularly well suited for use in intraosseous access procedures for at least the reasons discussed herein and/or for reasons that are otherwise apparent from the present disclosure.

For purposes of illustration, much of the disclosure herein pertains to creating a conduit or communication passageway to an interior of a bone structure by drilling through or otherwise penetrating hard, compact bone tissue to gain access to bone marrow or cancellous bone. Once access to an inner region of a bone is achieved, any variety of suitable procedures can be performed, such as, for example, infusion, aspiration, or extraction of bone marrow. Numerous situations can benefit from providing access to an interior of a bone in manners such as disclosed herein, such as, for example, when other methods of accessing a vein with an IV needle are difficult or in emergency situations, such as heart attack, burns, drug overdoses, etc., when rapid access to the vasculature of a patient via an interior of a bone may be desired. Other illustrative, non-limiting examples include bone marrow biopsy or bone marrow aspiration. The present disclosure is not, however, limited to these specific applications.

Certain known systems and methods for providing access to bone interior rely on a penetrator assembly that includes an outer penetrator and an inner trocar operable by a drill to penetrate the compact bone to gain access to the bone marrow. In order to initially make contact with the hard bone, it is often necessary to penetrate the skin and tissue that covers the bone. The prior methods use a sharp inner trocar in order to poke, puncture, or otherwise advance through the tissue. However, while the sharp tip of the trocar may be suitable for providing a passage through tissue, it can be suboptimal for initiating the cutting action through hard bone. In some instances, the sharp point effectively spins on the surface of the hard bone until the cutting edges of the trocar can become engaged with the hard bone.

Certain embodiments disclosed herein can be advantageous over at least the prior approaches just discussed. For example, in some embodiments, rather than using a sharp-tipped trocar that extends distally beyond cutting surfaces of the outer penetrator, a specialized needle having a distal cutting tip is used. The needle may be coupled with an obturator that does not extend beyond a distal face of the needle and is not involved in cutting or piercing the skin. The needle itself can have both the ability to cut or slice through the skin to reach bone, and can also readily bore through hard bone to the marrow. The obturator can prevent tissue debris from entering the needle lumen during insertion. These and/or other advantages of various disclosed embodiments will be apparent from the discussion that follows.

FIG. 1 is an exploded view of an embodiment of an intraosseous access system 100, with some components thereof shown in elevation and another shown in perspective. The intraosseous access system 100 can be used to penetrate skin and underlying hard bone for intraosseous access, such as, for example to access the marrow of the bone and/or a vasculature of the patient via a pathway through an interior of the bone.

In various embodiments, the system includes a driver 101 and an access assembly 109. The driver 101 can be used to rotate the access assembly 109 into a bone of a patient. In various embodiments, the driver 101 can be automated or manual. In the illustrated embodiment, the driver 101 is an automated driver 108. For example, the automated driver 108 can be a drill that achieves high rotational speeds.

The intraosseous access system 100 can further include an obturator assembly 102, a shield 105, and a needle assembly 202, which may be referred to, collectively, as the access assembly 109. The access assembly 109 may also be referred to as an access system. The obturator assembly 102 is referred to as such herein for convenience. In the illustrated embodiment, the obturator assembly 102 includes an obturator 104. However, in various other embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, etc. Accordingly, the obturator assembly 102 may be referred to more generally as an elongated medical instrument assembly. In like manner, the obturator 104 may be referred to more generally as an elongated medical instrument.

In the illustrated embodiment, the obturator assembly 102 includes a coupling hub 103 that is attached to the obturator 104 in any suitable manner (e.g., one or more adhesives or overmolding). The coupling hub 103 can be configured to interface with the driver 101, as further discussed below. The coupling hub 103 may alternatively be referred to as an obturator hub 103 or, more generally, as an elongated instrument hub 103.

In the illustrated embodiment, the shield 105 is configured to couple with the obturator 104. The coupling can permit relative longitudinal movement between the obturator 104 and the shield 105, such as sliding, translating, or other movement along an axis of elongation (i.e., axial movement), when the shield 105 is in a first operational mode, and can prevent the same variety of movement when the shield 105 is transitioned to a second operational mode. For example, as further discussed below, the shield 105 may couple with the obturator 104 in a manner that permits longitudinal translation when the obturator 104 maintains the shield 105 in an unlocked state, and when the obturator 104 is moved to a position where it no longer maintains the shield in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator, as further discussed below. In various embodiments, the shield 105 may be configured to rotate relative to the obturator 104 about a longitudinal axis of the obturator 104 in one or more of the unlocked or locked states.

With continued reference to FIG. 1, the needle assembly 202 is referred to as such herein for convenience. In the illustrated embodiment, the needle assembly 202 includes a needle 204. However, in various other embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In the illustrated embodiment, the needle assembly 202 includes a needle hub 203 that is attached to the needle 204 in any suitable manner. The needle hub 203 can be configured to couple with the obturator hub 103 and may thereby be coupled with the driver 101, as further discussed below. The needle hub 203 may alternatively be referred to as a cannula hub 203.

In the illustrated embodiment, the shield 105 is configured to couple with the needle hub 203. The coupling can prevent relative axial or longitudinal movement between the needle hub 203 and the shield 105, such as sliding, translating, or the like, when the shield 105 is in the first operational mode, and can permit the shield 105 to decouple from the needle hub 203 when the shield 105 is transitioned to the second operational mode. For example, as further discussed below, the shield 105 may couple with the needle hub 203 so as to be maintained at a substantially fixed longitudinal position relative thereto when the obturator 104 maintains the shield 105 in the unlocked state, and when the obturator 104 is moved to a position where it no longer maintains the shield in the unlocked state, the shield 105 may automatically transition to a locked state relative to the obturator 104, in which state the shield 105 also decouples from the needle hub 203.

As further discussed below, the shield 105 can be coupled with the obturator 104, the obturator 104 can be inserted into the needle 204, and the obturator hub 103 can be coupled to the needle hub 203 to assemble the access assembly 109. In the illustrated embodiment, a cap 107 may be provided to cover at least a distal portion of the needle 204 and the obturator 104 prior to use of the access assembly 109. For example, as further discussed below, in the illustrated embodiment, a proximal end of the cap 107 can be coupled to the obturator hub 103.

With continued reference to FIG. 1, the automated driver 108 may take any suitable form. The driver 108 may include a handle 110 that may be gripped by a single hand of a user. The driver 108 may further include an actuator 111 of any suitable variety via which a user may selectively actuate the driver 108 to effect rotation of a coupling interface 112. For example, the actuator 111 may comprise a button, as shown, or a switch or other mechanical or electrical element for actuating the driver 108. In the illustrated embodiment, the coupling interface 112 is formed as a socket 113 that defines a cavity 114. The coupling interface 112 can be configured to couple with the obturator hub 103. In the illustrated embodiment, the socket 113 includes sidewalls that substantially define a hexagonal cavity into which a hexagonal protrusion of the obturator hub 103 can be received. Other suitable connection interfaces are contemplated.

The automated driver 108 can include an energy source 115 of any suitable variety that is configured to energize the rotational movement of the coupling interface 112. For example, in some embodiments, the energy source 115 may comprise one or more batteries that provide electrical power for the automated driver 108. In other embodiments, the energy source 115 can comprise one or more springs (e.g., a coiled spring) or other biasing member that may store potential mechanical energy that may be released upon actuation of the actuator 111.

The energy source 115 may be coupled with the coupling interface 112 in any suitable manner. For example, in the illustrated embodiment, the automated driver 108 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage that mechanically transfers rotational energy from a mechanical (e.g., spring-based) energy source 115 to the gear assembly 117. The automated driver 108 can include a mechanical coupling 118 of any suitable variety to couple the gear assembly 117 with the coupling interface 112. In other embodiments, the gear assembly 117 may be omitted.

In various embodiments, the automated driver 108 can rotate the coupling interface 112, and thereby, can rotate the access assembly 109 at rotational speeds significantly greater than can be achieved by manual rotation of the access assembly 109. For example, in various embodiments, the automated driver 108 can rotate the access assembly 109 at speeds no less than 200, 300, 400, 500, 750, 1,000, 1,250, 1,500, 1,750, 2,000, 2,500, or 3,000 rotations per minute.

With reference to FIGS. 2 and 3, the obturator assembly 102, which includes the obturator hub 103 and the obturator 104, is shown in greater detail. In the illustrated embodiment, the obturator hub 103 includes a body or housing 120. A proximal end of the housing 120 can be coupled with (e.g., may be attached to or may itself define) a coupling interface 122 for coupling with the coupling interface 112 of the driver 101. In the illustrated embodiment, the coupling interface 122 is formed as a shaft 123 that is configured to be received within the cavity 114 of the socket 113 of the automated driver 108. In particular, the shaft 123 can interface with the socket 113 so as to be rotated thereby. In the illustrated embodiment, the shaft 123 defines a hexagonal cross-section that complements a hexagonal cross-section of the socket 113. Any other suitable arrangement is contemplated. In further embodiments, the socket 113, and the shaft 123 may be reversed, in that the driver 101 may include a shaft and the obturator hub 103 may define a socket for receiving the shaft of the driver 101.

The coupling interface 122 of the obturator hub 103 may further include a magnetic member 124, which may facilitate coupling with and/or may strengthen a coupling between the coupling interfaces 122, 112 of the obturator hub 103 and the driver 101, respectively. In various embodiments, the magnetic member 124 may include, for example, one or more of a ferromagnetic material and a ferromagnet. In some embodiments, the socket 113 may include a similar magnetic member that magnetically couples with the magnetic member 124. In other embodiments, the socket 113 itself may be formed as the magnetic member. For example, in some embodiments, the magnetic member 124 may comprise a magnet and the socket 113 may include a complementary magnetic member (not shown) at the base of the cavity 114. In other embodiments, the magnetic member 124 may comprise a magnet and the socket 113 may be formed of a magnetic material which the magnetic member 124 is attracted. In other embodiments, the magnetic member 124 may be omitted.

The body or housing 120 may further define a grip 126 that may facilitate manipulation of the obturator hub 103. For example, in the illustrated embodiment, the grip 126 is formed as an indented region of a sidewall 128 that spans a full perimeter of the housing 120.

The illustrated obturator hub 103 includes a skirt 130 that extends distally from a central portion of the housing 120. In the illustrated embodiment, the skirt 130 is defined by a distal portion of the sidewall 128. The skirt 130 can include one or more mechanical coupling members 131 that are configured to selectively couple the obturator hub 103 to the needle hub 203. In the illustrated embodiment, the skirt 130 includes two such mechanical coupling members 131 at opposite sides thereof. In particular, the illustrated embodiment includes two resilient arms or projections 132 that are capable of resiliently deforming in a lateral or radial direction. Each arm can include a snap interface, inward protrusion, or catch 134 at an internal side thereof that can interface with the needle hub 203 to achieve the coupling configuration.

In the illustrated embodiment, the obturator hub 103 further includes a pair of outward protrusions 136 that can assist in coupling the cap 107 to the obturator hub 103. For example, in some embodiments, the cap 107 can define an inner diameter only slightly larger than an outer diameter of the skirt 130. The outward protrusions 136 can slightly deform a proximal end of the cap 107 from a substantially cylindrical shape to a more oblong shape, which may enhance a grip of the cap 107 against the skirt 130. Any other suitable connection arrangement for the cap 107 is contemplated.

With reference to FIG. 3, the sidewall 128 can further define a coupling interface 137 configured to couple the obturator hub 103 to the needle hub 203 in a manner that causes the obturator hub 103 to rotate in unison with the needle hub 203. In the illustrated embodiment, the coupling interface 137 is formed as a socket 138 into which a shaft portion of the needle hub 203 can be received. The socket 138 can define a keyed shape that permits the obturator hub 103 to be coupled to the needle hub 203 in only one unique rotational or angular orientation. In particular, in the illustrated embodiment, the socket 138 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides. Any other suitable keying configuration is contemplated. As further discussed below, a keyed interface such as just described can ensure that the obturator 104 and the needle 204 are coupled to each other in a manner that may be desired, in some embodiments, such as to ensure that distal faces of both components are substantially parallel to each other and/or to otherwise ensure that a distal face of the obturator 104 is positioned in a desired manner relative to a distal face of the needle 204. For example, in some embodiments, the keyed interface ensures that the distal faces of the obturator 104 and the needle 204 are substantially parallel to each other and/or ensures that the distal face of the obturator 104 is fully recessed relative to the distal face of the needle 204.

With continued reference to FIG. 3, in some embodiments, the obturator 104 extends between a proximal end that is coupled to the obturator hub 103 and a distal end 142. The distal end 142 of the obturator 104 has a distal tip 146 at an extremity thereof. In the illustrated embodiment, the housing 120 of the obturator hub 103 substantially encompasses the proximal end 140 of the obturator 104.

The distal end 142 of the obturator 104 includes a distal face 147, which may, in various embodiments, alternatively be referred to as a cut face, ground face, or angled face. In some embodiments, the distal face 147 is formed as a bevel that is at an angle relative to a central longitudinal axis of the obturator 104. For example, in the illustrated embodiment, the distal face 147 defines a substantially planar bevel. In some embodiments, the distal face 147 of the obturator 104 may be configured to be recessed relative to a distal face of the needle 204

The beveled distal face 147 can be formed in any suitable manner, such as by grinding. For example, the distal face 147 that is substantially planar may be formed by a bias grind (which may also be referred to as a simple bias grind). As further discussed below, in some embodiments, the ground distal face 147 is formed (e.g., ground) at a distal end of a substantially cylindrical rod, and the rod is bent after the distal face 147 has been formed. In other embodiments, the cylindrical rod is bent before the distal face 147 is formed. In still other embodiments, a cylindrical rod is not bent, but rather, each of the distal face 147 and a curved or rounded region 148 adjacent thereto is instead formed by grinding. Other suitable processes for forming the distal end 142 of the obturator 104 are contemplated.

In some embodiments, the obturator 104 may be solid. For example, the obturator 104 may be devoid of passageways or openings extending through any portion thereof. Similarly, the distal end 142 of the obturator 104 may be substantially solid or closed, and may be devoid or openings or passageways therein or therethrough. The distal end 142 of the obturator 104 may substantially fill a lumen of the needle 204, or at least a distal portion of the lumen, to prevent skin or bone from entering into the needle 204 during an insertion event.

The obturator 104 may be formed of any suitable material, such as a substantially rigid material that can resist bending. The material can be sufficiently rigid and strong to inhibit tissue and/or bone from entering a lumen of the needle 204 during an access event. In various embodiments, the obturator 104 can comprise one or more of a rigid plastic or stainless steel. The obturator 104 may, in some instances, provide internal or structural support to the needle 204 during an insertion event. For example, the obturator 104 may act as a stiffener or stylet to inhibit bending of the needle 204 during drilling.

Figure 11A:
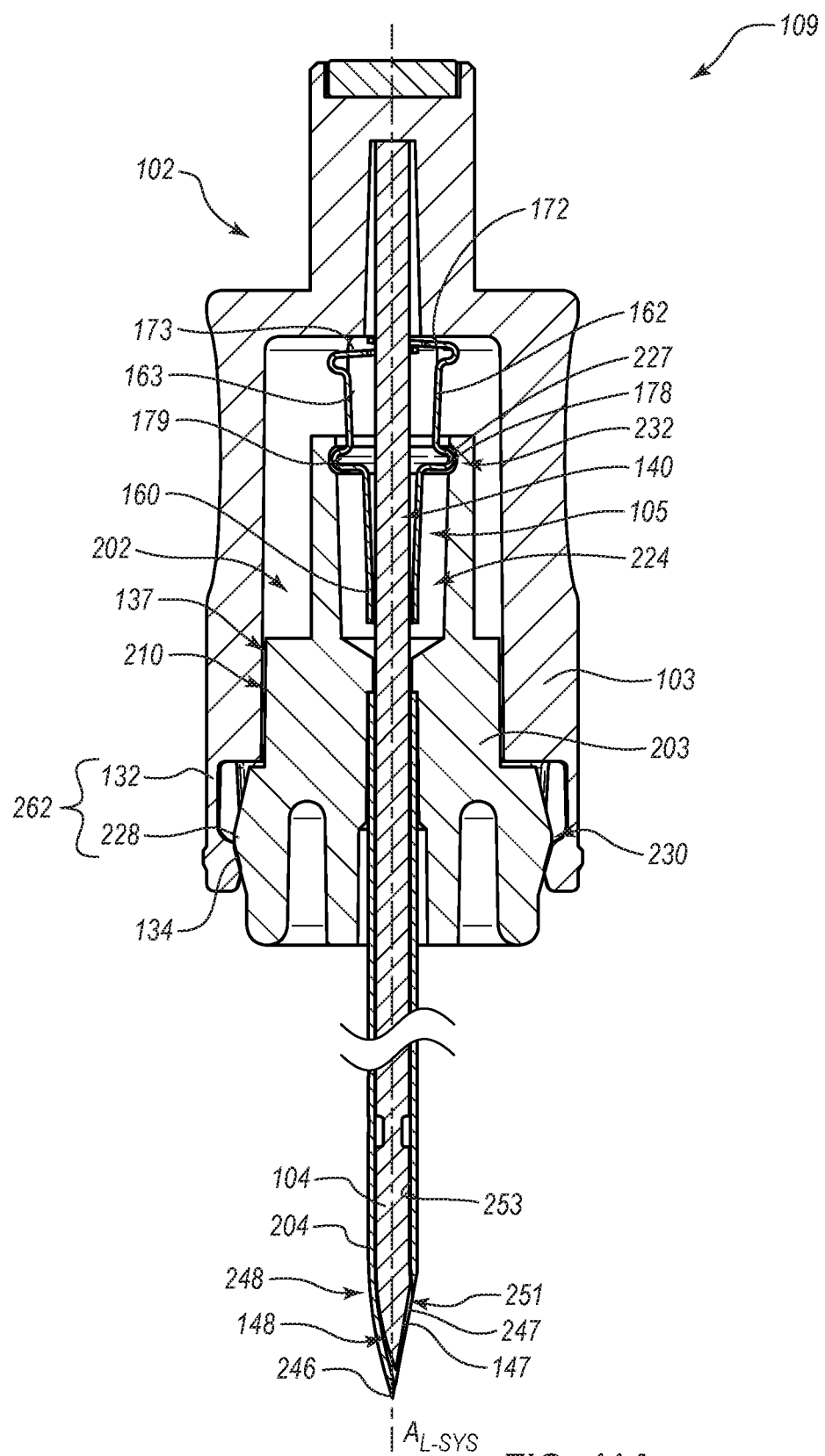
FIG. 11A depicts an early stage of an illustrative method of using the intraosseous access system of FIG. 1, and is a cross-sectional view of an access assembly portion of the intraosseous access system in an assembled state, the access assembly including the obturator assembly, the shield, and the needle assembly.

The distal end 142 of the obturator 104 may be shaped and sized to substantially fill a distal end of the needle 204 (see, e.g., FIG. 11A). In various embodiments, such an arrangement can inhibit bending or flattening of the distal end of the needle 204. For example, in some embodiments, there may be a close fit between an inner wall of the distal tip of the needle 204 and an outer surface of the distal end 142 of the obturator 104, and contact between these surfaces can permit the obturator 104 to reinforce the needle 204. For example, in the illustrated embodiment, the distal end 142 of the obturator 104 includes the curved region 148, which may also be referred to as a rounded, bent, or curved region or as a curved surface. A contour of the curved surface 148 can closely match a contour of an inner wall of the needle 204 at the distal end thereof (see, e.g., FIG. 11A). For example, in various embodiments, these curved surfaces may contact one another along a portion or substantially an entirety of length of the curved surface 148 of the obturator 104 and/or a portion or substantially an entire length of the inner curved surface of the distal end of the needle 204.

In other instances, a small space or gap may be present between the distal end 142 of the obturator 104 and the inner surface of the distal end of the needle 204. In certain of such arrangements, the distal end 142 of the obturator 104 may not initially provide resistance against bending of the needle tip. However, the obturator 104 may instead prevent the needle tip from bending beyond a preset amount. For example, upon bending of the needle tip such that the inner wall comes into contact with the distal end 142 of the obturator 104, the obturator 104 can stop or inhibit further bending of the needle tip.

In the illustrated embodiment, the obturator 104 may further include a recess 150. The recess 150 may be at a position that is between the proximal end and the distal end 142 of the obturator. Stated otherwise, the recess 150 may be positioned proximally relative to the distal tip 146 of the obturator 104. The recess 150 may be of any suitable variety, such as a groove, track, or any other suitable region of indentation or of reduced diameter or reduced thickness, as compared with, for example, a portion of the obturator 104 that is proximal to the recess 150. The recess 150 may or may not extend fully about a longitudinal axis of the obturator 104. In the illustrated embodiment, the recess 150 is defined as a groove 151 that extends fully about the longitudinal axis of the obturator.

Figure 4:
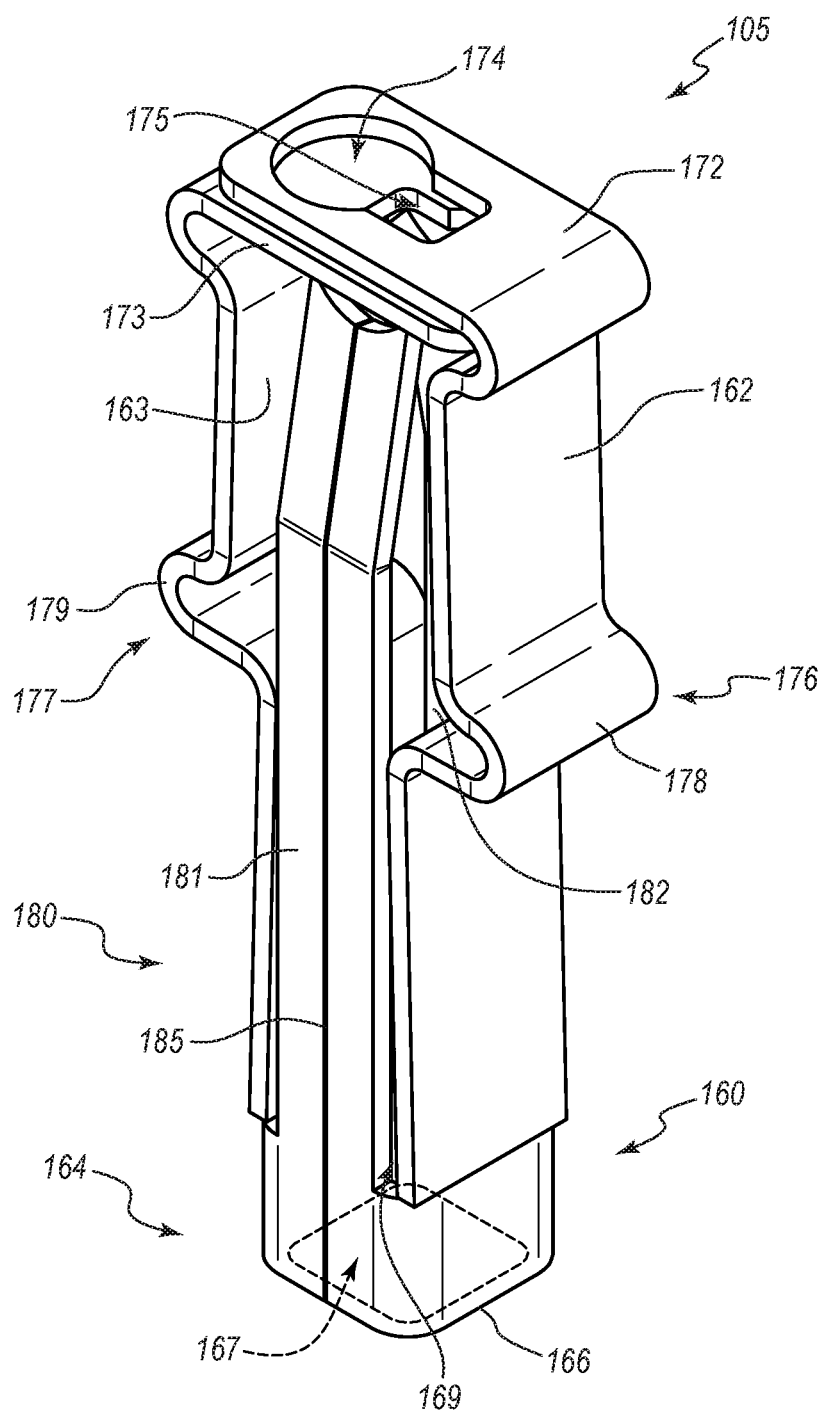
FIG. 4 is a perspective view of an embodiment of a shield portion of the intraosseous access system of FIG. 1.

FIG. 4 depicts a perspective view of an illustrative embodiment of the shield 105, which may also be referred to as, for example, a safety shield, guard, clip, cover, or stick-prevention element. The shield 105 includes a collar 160 and a pair of arms 162, 163. In the illustrated embodiment, the arms 162, 163 extend proximally from a proximal end of the collar 160. As further discussed below, the arms 162, 163 may be resiliently flexible members. The arms 162, 163 may be formed such that they are in a natural, resting, non-deflected, nondisplaced, nondeformed, undistorted, unflexed, or relaxed state when in the low-profile orientation depicted in FIG. 4, or are at least closer to such a low-energy state than then are when moved to an outwardly displaced state such as that depicted in FIGS. 11A, 11C, and 11D. For example, the arms 162, 163 may be deformed, displaced, flexed, or deflected laterally or radially outwardly away from a longitudinal axis of the shield 105 to achieve an orientation such as that depicted in FIGS. 11A, 11C, and 11D, which may give rise to an internal bias that naturally urges the arms 162, 163 back toward their natural state or toward a lower energy state.

The shield 105 can define a distal end 164 and a proximal end 165. In the illustrated embodiment, the collar 160 is positioned at the distal end 164 of the shield. The illustrated collar 160 defines a substantially rectangular transverse cross-section, although other configurations are contemplated. The collar 160 can define a distal tip 166 or distal edge of the shield 105. In the illustrated embodiment, the distal tip 166 includes a substantially planar face.

The collar 160 can define a distal opening 167 through which the obturator can pass. In various embodiments, the distal opening 167 may define a fixedly open configuration. Stated otherwise, in some embodiments, the opening 167 is configured to remain open even after the distal tip 146 of the obturator 104 has been drawn into the shield 105. In other terms, the collar 160 may be substantially nondeformable or may define a single shape throughout full operation of the shield 105.

As further discussed below, in some embodiments, the collar 160 is capable of inhibiting or preventing undesired contact with the distal tip 146 of the obturator 104, although the distal opening 167 remains open when the shield 105 is locked onto the obturator 104. For example, the distal opening 167 may be sized to prevent the skin of a user or other individual from entering into a cavity 169 of the shield 105 to a sufficient distance to come into contact with the distal tip 146 of the obturator 104.

In the illustrated embodiment, the cavity 169 is generally defined by the collar 160, distal ends of the arms 162, 163, and a pair of panels 181, 182. Stated otherwise, a cage 180 or receptacle may be defined by the collar 160, the arms 162, 163, and the panels 181, 182. The cage 180 can prevent inadvertent contact with the distal tip 146 of the obturator 104 when the distal tip 146 has been drawn into and is being retained therein.

In the illustrated embodiment, the panels 181, 182 may also be referred to as deflection arms or retainers (e.g., arms 181, 182). Similar to the arms 162, 163, the arms 181, 182 can be naturally biased to the natural configuration shown in FIG. 4 in which the arms 181, 182 are angled inwardly, in a distal-to-proximal direction, toward a longitudinal axis of the shield 105. The arms 181, 182 can be deflected outwardly by a proximal portion of the obturator 104, and the proximal tips of the arms 181, 182 can naturally spring inwardly into the groove 151 as the obturator 104 is drawn proximally through the shield 105.

In the illustrated embodiment, at the proximal end 165 of the shield 105, the arms 162, 163 define lateral extensions 172, 173, respectively, which may extend in opposite directions. The lateral extensions 172, 173 can define openings 174, 175 through which the obturator 104 can pass. The openings 174, 175 can be key shaped with enlarged regions that permit ready passage of the obturator 104 and narrowed portions that are configured to enter into the groove 151 of the obturator 104 to lock, delimit, inhibit, or prevent axial movement between the shield 105 and the obturator 104. In the illustrated embodiment, the openings 174, 175 are shaped substantially identical to each other, but are oriented in opposite directions. The enlarged portions of the openings 174, 175 are shaped substantially as semicircles, and the constricted portions of the openings 174, 175 are shaped substantially as rectangles. Other configurations are contemplated.

In some embodiments, one or more of the arms 162, 163 can define one or more connection interfaces 176, 177, respectively, that can engage the needle hub 203, as discussed further below. In the illustrated embodiment, the connection interfaces 176, 177 are directed outwardly so as to engage the needle hub 203 when the arms are deformed or distorted outwardly and are held in this outward orientation by the larger diameter portion of the obturator 104. In the illustrated embodiment, the connection interfaces 176, 177 are formed as outwardly directed protrusions 178, 179. For example, in the illustrated embodiment, the protrusions 178, 179 are formed as outward bends in the arms 162, 163, respectively.

In various embodiments, the shield 105 may be formed of a unitary monolithic piece of material, or stated otherwise, may have a single-piece construction. For example, in some embodiments, the shield 105 may be formed of a single piece of sheet metal (e.g., stainless steel) that has been folded and/or bent into the configuration depicted in FIG. 4. For example, in the illustrated embodiment, the shield 105 is folded into a substantially rectangular form at four primary bends, one at each corner of the collar 160. Additional bends (in some instances, two bends each) yield each of the lateral extensions 172, 173. In some embodiments, the additional bends (in some instances, three bends each) yield the outward protrusions 178, 179. Upon folding or bending the single sheet of metal, opposite edges of the sheet may be in contact or in close proximity with each other along a seam 185. In the illustrated embodiment, the seam 185 extends longitudinally along the arm 181. In other embodiments, the seam 185 may instead be located at one of the bends of the collar 160, so as not to be present along or through any of the arms 162, 163, 181, 182.

In other embodiments, the shield 105 may be injection molded, 3D-printed, or formed in any other suitable manner. In other or further embodiments, the shield 105 may be formed of multiple pieces that are joined together.

Figure 6:
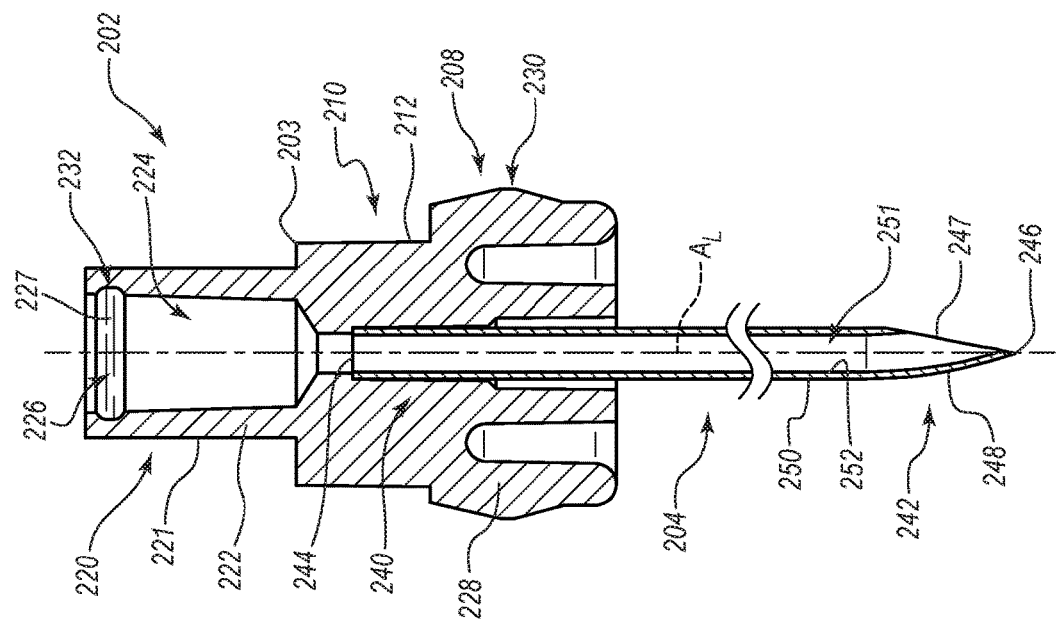
FIG. 6 is a cross-sectional view of the needle assembly taken along the view line 6-6 in FIG. 5.
Figure 5:
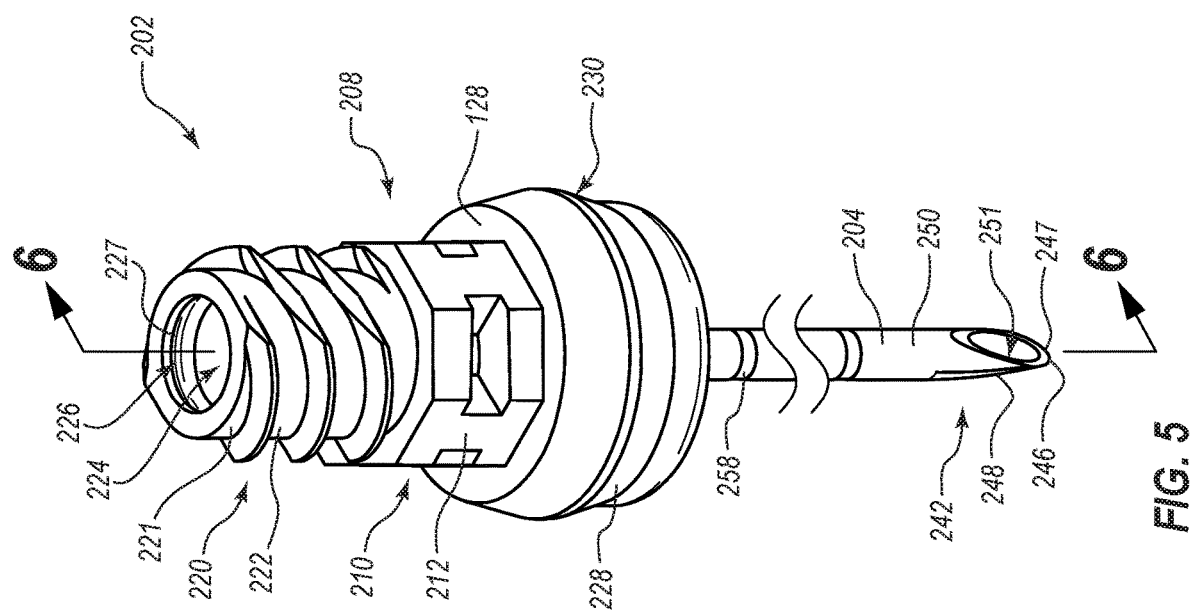
FIG. 5 is a perspective view of an embodiment of a needle assembly portion of the intraosseous access system of FIG. 1.

With reference to FIGS. 5 and 6, as previously discussed, the needle assembly 202 can include the needle hub 203 and the needle 204, which can be fixedly secured to each other in any suitable manner (e.g., one or more adhesives or overmolding). Further, as previously discussed, the needle hub 203 and the needle 204 may more generally be referred to as a cannula hub and as a cannula, respectively.

In the illustrated embodiment, the needle hub 203 includes a housing or body 208. The body 208 can define a coupling interface 210 that is configured to couple with the coupling interface 137 of the obturator hub 102 (see FIG. 3). For example, the coupling interface 210 can be formed as a shaft 212 that is configured to be received within the socket 138 of the obturator hub 102 (see FIG. 3). As shown in FIG. 5, in some embodiments, the shaft 212 can define a keyed shape that permits the needle hub 203 to be coupled to the obturator hub 103 in only one unique rotational or angular orientation. In particular, in the illustrated embodiment, the shaft 212 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides. The prism shape may be substantially the same as that defined by the coupling interface 137, but with slightly shorter sides. Any other suitable keying configuration is contemplated.

The needle hub 202 can further include a connector 220, e.g., a medical connector, of any suitable variety. The connector 220 may be defined by the housing 208 and may extend proximally from the shaft 212. The connector 220 can be configured to couple with any suitable medical equipment, such as for infusing fluid into a patient, after the needle 204 has been inserted into bone. For example, in the illustrated embodiment, the connector 220 is formed as a Luer fitting 221 (i.e., a female Luer fitting). The illustrated Luer fitting 221 includes a sidewall 222 that defines a cavity or lumen 224. In some embodiments, a portion of a male Luer fitting may be received within the lumen 224 when the needle hub 202 is in use. The lumen 224 of the connector 220 can be in fluid communication with a lumen 251 of the needle 204, which is discussed further below.

In the illustrated embodiment, the sidewall 222 defines a connection interface 226 that is configured to couple the needle hub 202 with the shield 105 when the shield 105 is in the unlocked state relative to the obturator 104. In this state, the shield 105 may also be termed to be in a locked or engaged state relative to the needle hub 202. For example, in the illustrated embodiment, the connection interface 226 is formed as an annular groove 227 within which the outward protrusions 178, 179 of the shield 105 (see FIGS. 4, 11A, and 11D) can be received to prevent the shield 105 from moving in at least a longitudinal direction relative to the needle hub 202.

The housing 208 may further define a skirt 228, which may extend distally from the shaft 212. The skirt 228 may also extend outwardly relative to the shaft 212. The skirt 228 may define a maximum transverse perimeter 230 of the hub 202. In the illustrated embodiment, the maximum transverse perimeter 230 is substantially circular. The maximum transverse perimeter 230 represents an outline of the needle assembly 202 when the assembly 202 is viewed from above or below, or stated otherwise, is viewed along a longitudinal axis of the needle assembly 202.

With reference to FIG. 6, an upper interior region of the sidewall 222 can define a maximum transverse perimeter 232 of the lumen 224. In the illustrated embodiment, the maximum transverse perimeter 232 is substantially circular. In other embodiments, the maximum transverse perimeter 232 may be defined by a portion of the sidewall 222 that is positioned further down, within the lumen 224, and may not, for example, be visible in a top plan view of the needle hub 203. In still other embodiments, the maximum transverse perimeter 232 represents an outline of the lumen 224 when the assembly 202 is viewed from above, or stated otherwise, is viewed along a longitudinal axis of the needle assembly 202.

With continued reference to FIG. 6, the needle 204 can include a proximal end 240 and a distal end 242. The proximal end 240 terminates at a proximal tip 244, and the distal end 242 terminates at a distal tip 246. The distal tip 246 may also be referred to as the distalmost point of the needle 204. The proximal end 240 can be fixedly secured to the housing 208 in any suitable manner. The needle 204 may be formed of any suitable material. For example, in some embodiments, the needle 204 is formed of stainless steel, such as 304 stainless steel, 316 stainless steel, or any other suitable grade of stainless steel (e.g., such as may be used for hypodermic needles). The material may desirably be sufficiently rigid to pierce a tissue layer and penetrate hard bone.

Figure 7:
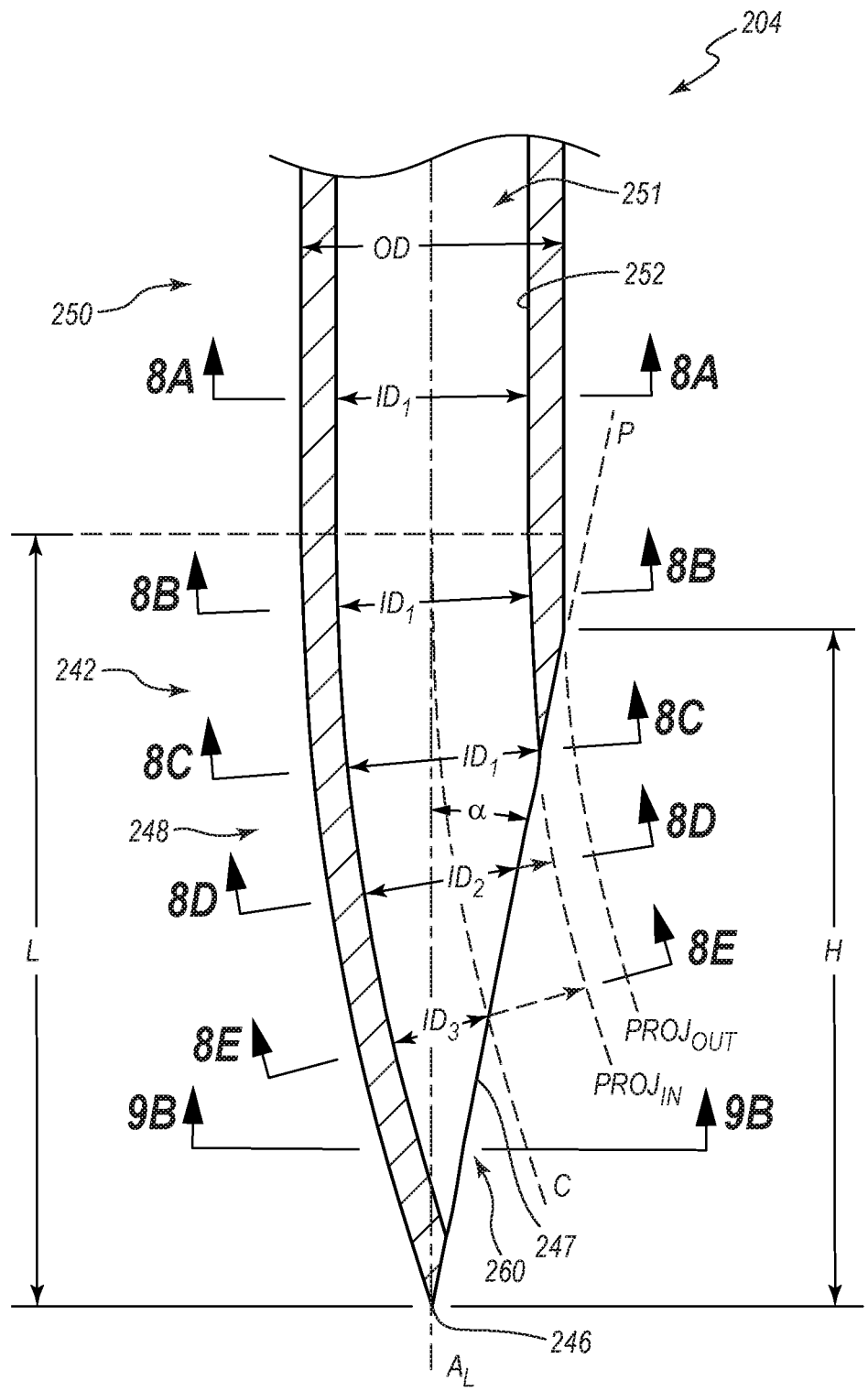
FIG. 7 is an enlarged cross-sectional view of a distal end of a needle of the needle assembly.

With reference to FIGS. 6 and 7, the distal end 242 of the needle 204 can include a distal face 247, which may, in various embodiments, alternatively be referred to as a cut face, ground face, or angled face. In some embodiments, the distal face 247 is formed as a bevel that is at an angle relative to a central longitudinal axis $A_L$ of the needle 204, which can correspond to an axis of rotation of the needle 204 during an insertion event. For example, in the illustrated embodiment, the distal face 247 defines a substantially planar bevel. The plane of the bevel is identified as P in FIG. 7. The beveled distal face 247 can be formed in any suitable manner, such as by grinding. For example, the distal face 247 that is substantially planar may be formed by a bias grind (which may also be referred to as a simple bias grind). As further discussed below, in some embodiments, the ground distal face 247 is formed (e.g., ground) at a distal end of a substantially cylindrical tube, and the tube is bent after the distal face 247 has been formed. In other embodiments, the cylindrical tube is bent before the distal face 247 is formed.

With reference to FIG. 7, the illustrated distal face 247 is at an angle α relative to the central longitudinal axis $A_L$. Any suitable value of the angle α is contemplated. For example, in various embodiments, the angle α is within a range of from about 8 degrees to about 20 degrees; is no less than about 8, 10, 15, or 20 degrees; or is no greater than about 8, 9, 10, 15, or 20 degrees. In some embodiments, the angle α is approximately 11 degrees.

As shown in FIG. 11A, in the illustrated embodiment, when the obturator 104 is fully inserted into the needle 204, the distal face 147 thereof is slightly recessed relative to the distal face 247. The distal face 147 may be substantially parallel to the distal face 247 of the needle 204, or it may be oriented at a small angle relative to the distal face 247, the angle having a value no greater than about 1, 2, 3, 4, 5, or 10 degrees. Moreover, central longitudinal axes of each of the obturator 104 and the needle 204 can be aligned or colinear, and may correspond with a central longitudinal axis $A_{L-SYS}$ of the access system or access assembly 109, which may also be the axis of rotation of the access assembly 109. In some embodiments, the distal face 147 may define an angle relative to the central longitudinal axis that is no greater than about 8, 9, 10, 15, or 20 degrees. In some embodiments, such as certain embodiments for which the angle α defined by the distal face 247 of the needle 204 is approximately 11 degrees, the angle defined by the distal face 147 of the obturator 104 is approximately 9.5 degrees.

With reference to FIGS. 7 and 9, the distal end 242 of the needle 204 can include a curved or rounded region 248, which can be joined to an edge of the distal face 247 and can extend away therefrom about a periphery of the distal end 242. In a plane that passes through the longitudinal axis $A_L$ of the needle 204 and that is perpendicular to the plane P defined by the distal face 247 (i.e., the plane of the page in FIG. 7), a tangent TAN to the rounded region 248 at or adjacent to the distal tip 246 can define an angle β relative to the longitudinal axis $A_L$. Any suitable value of the angle β is contemplated. In some instances, the angle β is approximately the same as or slightly larger than the angle α. Together, the angles α and β may be sufficiently small to provide a sharp distal tip 246 that can readily slice through skin. For example, in various embodiments, the angle β is within a range of from about 8 degrees to about 25 degrees; is no less than about 8, 10, 15, 20, or 25 degrees; or is no greater than about 8, 9, 10, 15, 20, or 25 degrees. In some embodiments, the angle β is approximately 15 degrees. In various embodiments, the angles α and β combined (or stated otherwise, a slicing angle of the distal tip 246) are no greater than 15, 20, 25, 30, 35, or 40 degrees.

When the needle 204 is advanced in a distal direction, the sharp distal tip 246, as defined by the distal face 247 and the rounded region 248, can permit the distal end 242 of the needle 204 to readily pierce or cut through tissue. For example, in some instances, the distal end 242 of the needle 204 can be advanced distally, substantially without rotation about the axes $A_L$, $A_{L-SYS}$ and can slice through tissue, such as in a manner similar to a scalpel. The distal tip 246 may ultimately come into contact with bone, at which point the needle 204 may be rotated to cut through the bone.

With reference again to FIGS. 6 and 7, in the illustrated embodiment, the needle 204 includes a shaft 250 that is fixedly secured to the hub 203 at its proximal end. The shaft 250 extends distally and terminates where the distal end 242 of the needle 204 begins. In the illustrated embodiment, a boundary between the distal end of the shaft 250 and a proximal end of the distal end 242 of the needle is illustrated by a horizontal broken line in FIG. 7. The distal end 242 of the needle 204 extends downwardly from this boundary terminates at the distal tip 246. As shown in FIG. 5, an exterior surface of the shaft 250 can include one or more depth markers 258 of any suitable variety.

In the illustrated embodiment, the needle shaft 250 is substantially cylindrical, at each of an interior and an exterior surface thereof. The needle shaft 250 may also be said to define circular lateral inner and outer cross-sections (which may also be referred to as a transverse cross-sections), each having a constant diameter along a full longitudinal length of the shaft 250. Other arrangements are also contemplated. For example, in some embodiments, the shaft 250 may be shaped substantially as a frustocone, and may have a very gradual taper, such that a diameter of one or more of its inner or outer circular cross-sections decreases in the distal direction. However, in some instances, it can be desirable for the needle shaft 250 to have a substantially cylindrical outer surface, as this may inhibit or prevent the needle 204 from backing out of the bone after implantation, and may likewise inhibit or prevent extravasation at the insertion site.

In the illustrated embodiment, the distal end 242 of the needle 204 does not define a constant lateral outer cross-sectional area, relative to the longitudinal axis $A_L$, along a full length thereof. For example, as can be seen in FIG. 7, the rounded region 248 and the distal face 247 taper toward the distal tip 246. It may be said that the needle tip 246 is bent towards the central longitudinal axis $A_L$ of the needle 204. As a contour of the rounded region 248 is followed in a distal direction, the contour continuously approaches closer to the central longitudinal axis $A_L$ of the needle 204. As further discussed below, the distal tip 246 can be positioned on or near the central longitudinal axis $A_L$ of the needle 204, as depicted in the illustrated embodiment.

In the illustrated embodiment, the distal end 242 of the needle 204 does, however, define a constant, or substantially constant, lateral inner cross-sectional area relative to a center line C that passes through a center of the lumen 251 along a significant length of the distal end 242. The lumen 251 is defined by an interior surface 252 of the needle 204, and the center line C can be defined as a line that extends through a center of each plane that is delimited by the interior surface 252 and that contacts the interior surface 252 at right angles about a full periphery of the plane. According to this definition, the center line C terminates when a transverse plane therethrough contacts the upper end of a distal opening 260 of the lumen 251. That is, in FIG. 7, according to the foregoing definition of the center line C, the center line C terminates at the position of the cross-sectional plane demarcated by the view lines 8C-8C. This is because, below this point, no plane that contacts the interior surface 252 at right angles is fully delimited by the interior surface 252, due to the presence of the opening 260.

In further embodiments, the interior surface 252 can be projected outwardly through the distal opening 260 of the needle 204, as depicted by the broken lines labeled $PROJ_{IN}$ in FIGS. 7, 8D, and 8E. In some instances, depending on a manner in which the needle 204 has been formed, this projected surface can correspond to the interior surface of a portion of a tubular element that was ground away during formation of the distal end 242 of the needle 204. In some instances, the center line C can be defined as a line that extends through a center of each plane that is delimited by one or both of the interior surface 252 and the projection $PROJ_{IN}$ and that contacts one or both of the interior surface 252 and the projection $PROJ_{IN}$ at right angles about a full periphery of the plane. In the illustrated embodiment, a lateral inner cross-sectional area A (FIGS. 8A-8E) defined by both the interior surface 252 and its projection $PROJ_{IN}$, relative to the center line C, can be substantially constant along a full length of the distal end 242, as shown in FIGS. 7 and 8A-8E. In various embodiments, the lateral inner cross-sectional area A, which is defined relative to the center line C (according to either or both of the definitions of the center line C provided above), varies along a full length of the needle by no more than 5, 10, 15, 20, 25, 30, 35, 40, 45, or 50 percent of a maximum value of the area A.

In some embodiments, it can be advantageous to have a relatively large or unencumbered lumen 251 along a full length of the needle 204 and/or along a length of the needle the extends proximally from the distal opening 260. For example, in some instances, such a large or unobstructed passage can facilitate or enable use of the obturator 104, whether in general or, more particularly, for use as a stiffener. In other or further instances, such a passage can permit relatively high flow rates for infusion or aspiration via the lumen 251, or in other instances, can avoid introducing resistance or restraint in a system that may already be limited, restrained, or constrained. For example, in some instances, such as in certain emergency situations, it may be desirable to deliver drugs in solution into the vasculature of the patient via the lumen 251, which provides a pathway into a bone of the patient. In such circumstances, a practitioner may couple a drug delivery (e.g., IV) bag to the needle 204 and squeeze the bag to force the solution into the bone of the patient. The bone and/or the internal structure thereof and/or native pressure therein may limit how quickly the solution may be introduced into the bone via this approach. Accordingly, it may be desirable to reduce any further constriction of the system, such as may otherwise result from a partially blocked or constricted lumen 251. In other or further instances, it may be desirable for the needle 204 to have a relatively small outer diameter OD, such as to reduce discomfort to patient and/or to facilitate healing of skin and bone tissue after a procedure. However, in still further applications, it can be desirable for the needle 204 to be sufficiently large to have sufficient columnar strength to withstand the static and inertial loads provided thereto during an insertion event. In various embodiments, providing the needle 204 with a relatively large and/or relatively unobstructed lumen 251 can achieve or balance some or all of the foregoing goals, dependent upon intended use of the needle 204.

In various embodiments, the OD of the needle 204 can be no less (i.e., no larger than) than 17, 16, 15, 14, or 13 gauge. Stated otherwise, in various embodiments, the OD of the needle can be no greater than about 58, 65, 72, 83, or 95 thousandths of an inch (about 1.5, 1.7, 1.8, 2.1, or 2.4 millimeters). In some embodiments, the OD is about 15 gauge (about 72 thousandths of an inch, or about 1.8 millimeters). Other sizes are also possible. For example, in some instances, the foregoing sizes may be advantageous for infusion applications, whereas larger sizes may be desired for certain biopsy or aspiration applications.

In certain embodiments, such as various embodiments having an OD within the size ranges just discussed, a thickness of the sidewall of the needle 204 can be no greater than 5, 10, 15, or 20 thousandths of an inch. In some embodiments in which the OD is about 15 gauge (about 72 thousandths of an inch), the wall thickness can be no greater than about 10 thousands of an inch.

In certain embodiments, such as various embodiments having an OD and/or a wall thickness within the size ranges just discussed, the needle 204 can permit a flow rate of about 1 liter per hour (such as for infusion into a tibia) or a flow rate of about 4 liters per hour (such as for infusion into a humerus). The needle 204 may further be capable of withstanding fluid delivery at the foregoing rates over a wide variety of pressures, such as may result from a practitioner squeezing on an IV bag or the like.

Figure 9A:
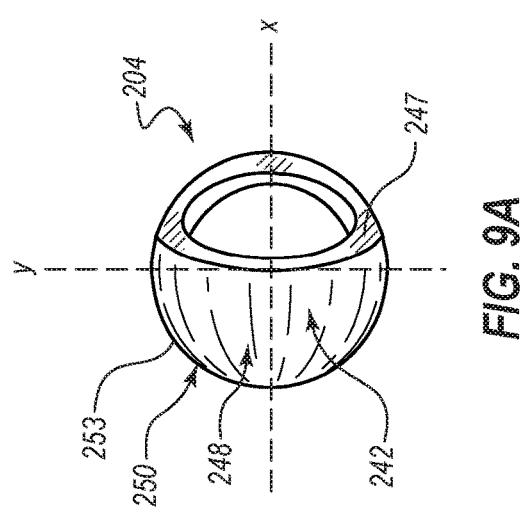
FIG. 9A is an enlarged plan view of the distal end of the needle.
Figure 9B:
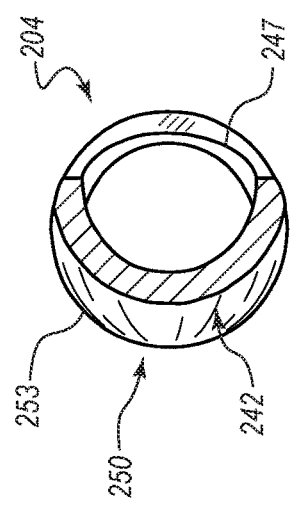
FIG. 9B is a cross-sectional view of the needle taken along the view line 9B-9B in FIG. 7.

With reference to FIGS. 7, 9A and 9B, as previously mentioned, in the illustrated embodiment, an outer surface of the shaft 250 is substantially cylindrical, whereas an outer surface of the distal end 242 is not. Accordingly, the needle 204 defines a lateral outer cross-section (relative to the longitudinal axis $A_L$) that is substantially circular along the full longitudinal length of the shaft 250 (see, e.g., FIG. 8A). Moreover, the substantially circular outer cross-section defines an outer diameter OD that is substantially constant along a full longitudinal length of the shaft 250. In some embodiments, it can be desirable for the distal end 242 of the needle 204 to have a lateral outer cross-section, relative to the longitudinal axis $A_L$ (corresponding to the axis of rotation), that is no larger than the circular lateral outer cross-section of the shaft 250. For example, as seen in FIGS. 9A and 9B, the cylindrical external surface of the shaft 250, which is substantially circular in an end-on view, is not obstructed from view by any portion of the distal end 242 of the needle 204. Stated otherwise, the external surface of the shaft 250 can define a lateral or transverse perimeter 253, which in some embodiments is substantially the same at any cross-sectional plane that extends orthogonally through the longitudinal axis $A_L$, and in the illustrated embodiment, the lateral perimeter 253 is substantially circular. As used herein, the term "substantially circular" means that a shape exhibits a generally circular or oval profile and that a maximum diameter thereof is no greater than 10 percent larger than a minimum diameter thereof. In the illustrated embodiment, when the needle 204 is rotated to bore a hole, such as through hard bone, the shaft 250 can snugly fit within the bore.

Relationships between the shaft 250 and the distal end 242 (or cutting portion) of other or further embodiments of the needle 204 can be described in other terms. Such needles 204 may also be capable of creating a bore with the distal end 242 that is dimensioned so as to permit a snug reception of the shaft 250. For example, in some embodiments, along a full longitudinal length of the distal end 242, each lateral (relative to the longitudinal axis $A_L$) outer cross-section of the distal end 242 can be fully or partially circumscribed by the smallest lateral outer cross-section of the shaft 250. In other or further embodiments, a maximum width (e.g., diameter) of each lateral outer cross-section of the distal end 242 can be no larger than the smallest outer dimension (e.g., outer diameter) of the shaft 250, such as at the distal end of the shaft 250. In certain embodiments, no portion of each lateral outer cross-section of the distal end 242 extends beyond (i.e., extends laterally outwardly beyond) a lateral outer cross-sectional profile of at least a distal portion of the shaft 250.

In some embodiments, such as in the illustrated embodiment, it may be stated that at no position along a full longitudinal length of the needle 204 does the outer surface of the needle extend beyond a perimeter of a lateral outer cross-section of the shaft 250. In some embodiments, such as in the illustrated embodiment, it may be stated that at no position along a full longitudinal length of the distal end 242 of the needle 204 does the outer surface of distal end 242 extend laterally outwardly beyond a perimeter of a lateral outer cross-section of the shaft 250. Stated otherwise, at every position along a full longitudinal length of the distal end 242 of the needle 204, the outer surface of the distal end 242 extends laterally outwardly relative to the longitudinal axis $A_L$ no further than does a lateral or transverse perimeter 253 of the outer surface of the shaft 250, e.g., the perimeter at a distalmost end of the shaft 250 along a plane that is orthogonal to the longitudinal axis $A_L$ (see FIGS. 9A and 9B).

In certain embodiments, the distal end 242 of the needle 204 may define a constant, or substantially constant, lateral outer cross-sectional area relative to the center line C that passes through a center of the lumen 251 and/or the projection $PROJ_{IN}$ thereof. In further embodiments, the exterior surface of the needle 204 can be projected in a similar manner to the inner projection PROJ/N, as depicted by the broken lines labeled $PROJ_{OUT}$ in FIGS. 7, 8D, and 8E. In some instances, depending on a manner in which the needle 204 has been formed, this projected outer surface can correspond to the outer surface of a portion of a tubular element that was ground away during formation of the distal end 242 of the needle 204. In the illustrated embodiment, a lateral outer cross-sectional area (FIGS. 8A-8E) defined by both the exterior surface and its projection $PROJ_{OUT}$, relative to the center line C, can be substantially constant along a full length of the distal end 242, as shown in FIGS. 7 and 8A-8E. In various embodiments, the lateral outer cross-sectional area, which is defined relative to the center line C (according to either or both of the definitions of the center line C provided above), varies along a full length of the needle by no more than 5, 10, 15, 20, 25, 30, 35, 40, 45, or 50 percent of a maximum value thereof.

Similarly, as shown in FIGS. 8A-8E, the outer diameter OD may be substantially along the center line C. In various embodiments, the outer diameter OD may vary along a full length of the needle by no more than 5, 10, 15, 20, 25, 30, 35, 40, 45, or 50 percent of a maximum value thereof.

With continued reference to FIGS. 8A-8E, a series of outer transverse cross-sectional perimeters 261A-261E, relative to the center line C in FIG. 7, are shown. In these images, the outermost perimeter 261A-261E of the needle 204 at each cross-sectional plane appears substantially circular (FIGS. 8A-8C) or substantially semicircular (FIGS. 8D and 8E). In various embodiments, at least a portion of one or more of the outer perimeters 261B-261E of the distal end 242 are deformed slightly from being perfectly circular or perfectly semicircular, however. For example, as further discussed below, in some instances, formation of the distal end 242 may involve clamping, crimping, compressing, or otherwise constraining or otherwise shaping the distal end 242 to ensure that no portion thereof extends transversely outwardly (relative to the longitudinal axis $A_L$) beyond the outer periphery 261A of the shaft 250. This process may deform at least a portion of the outer and/or inner surfaces of the distal end 242 of the needle 204 to slightly deviate from defining a true circle or a true semicircle within cross-sectional planes that are transverse to the center line C.

With continued reference to FIGS. 8A-8E, with respect to the inner surface 252 of the needle 204, the transverse inner perimeter, relative to the center line C (see FIG. 7), may be substantially circular or substantially semicircular. For example, in each of FIGS. 8A, 8B, and 8C, the inner diameters in two mutually orthogonal directions are substantially equal to each other. That is, the inner diameters depicted in FIGS. 8A, 8B, and 8C are all substantially equal and thus are each identified as $ID_1$. In some embodiments, however, one of the diameters (e.g., the vertically oriented diameter in the illustrated view) may be slightly smaller than the other diameter (e.g., the horizontally oriented diameter in the illustrated view) in one or more of FIG. 8B or 8C due to slight deformations of the tube during formation of the distal end 242. Nevertheless, the cross-sectional profile may remain substantially circular.

Similarly, in FIGS. 8D and 8E, in which the inner perimeters of the surface 252 are delimited by the distal face 247 of the needle 204, the inner diameter of the inner perimeter in one dimension may be substantially the same as in more proximally located regions of the needle 204. For example, the vertically oriented diameter in the illustrated view for each of FIGS. 8D and 8E is identified as $ID_1$. In some embodiments, however, these vertically directed diameters, in the illustrated views, may be slightly smaller than similarly oriented diameters of more proximal portions of the distal end 242, such as at the positions of one or more of FIG. 8B or 8C, due to slight deformations of the tube during formation of the distal end 242. Nevertheless, the cross-sectional profile may remain substantially semicircular.

In some embodiments, the substantially circular geometries of the needle 204, as described above, can advantageously resist buckling, bending, or folding over of the distal end 242 as the needle 204 is pressed against bone during an insertion event and/or spun at high rates. For example, the distal end 242, or any portion thereof, is far less prone to buckling, bending, or folding over due to the geometries described above, as compared with certain arrangements that may have, for example, a thinner, flatter, and/or more oval-shaped profile. This can be demonstrated, for example, from an application of Euler's critical load formula, in which the critical load that can be borne by a column is directly proportional to the minimum area moment of inertia of the cross-section of a column. For a given maximum outer diameter of a column—in this case, the distal end 242 of the needle 204, either considered alone or considered collectively with at least a portion of the shaft 250, circular geometries are less prone to buckling, as compared to thinner, flatter, and/or more oval-shaped profiles, due to the symmetries of the area moments of inertia for the circular geometries. Thus, for example, with reference to FIG. 9A, due to the substantially circular geometries discussed above, the distal end 242 can have approximately the same resistance to buckling about the y-axis as it does about the x-axis.

With reference again to FIG. 7, the distal face 247 can define a longitudinal height H, which can be the longitudinal component of a maximum length of the face 247, or stated otherwise, is the distance the face 247 extends longitudinally. In various embodiments, the longitudinal height H is about 0.1, 0.15, 0.2, 0.25, or 0.3 inches; is no greater than about 0.1, 0.15, 0.2, 0.25, or 0.3 inches, or is no less than about 0.1, 0.15, 0.2, 0.25, or 0.3 inches. Any other suitable height is possible.

The longitudinal height H of the distal face 247 may be a significant percentage of the overall longitudinal length L of the distal end 242. In various embodiments, the longitudinal height H of the distal face 247 may be no less than about 50, 60, 70, 80, or 90 percent of the longitudinal length L of the distal end 242. In some embodiments, the longitudinal height H of the distal face 247 may be substantially equal to the longitudinal length L of the distal end 242.

The rounded region 248 can extend along the full longitudinal length L of the distal end 242. The radius of curvature of the rounded region 248 can be relatively large, or stated otherwise, the deflection of the outer surface of the distal end 242 toward the longitudinal axis $A_L$ can be gradual. Such an arrangement can contribute to the sharpness of the distal tip 246 and facilitate insertion of the needle 204 through skin tissue. In other or further instances, such an arrangement can be relatively resistant to bending, folding over, or buckling, due to an only slight deviance of the center line C (which passes through the center of the circular geometries) from the longitudinal axis $A_L$ of the needle 204. For example, a static load can be applied along the axis $A_L$ of the needle 204 as a practitioner presses downwardly or distally on the automated driver 108 and as the distal tip 246 of the needle presses against the bone. The full length of the needle 204 bears this load, and the stable circular geometry that extends along this full length, with only minor deviance therefrom at the distal end 242, permits the needle 204 to bear the load without buckling (e.g., at a center of the needle 204, or elsewhere). The circular configuration can similarly be resistant to inertial loads that result from high rotational speeds of the needle 204.

In various embodiments, the length of the rounded region 248 (which in the illustrated embodiment is equal to L) is no less than about 2, 2.5, 3, 3.5 or 4 times that of the OD of the shaft 250. In some embodiments, the OD is approximately 72 thousandths of an inch, and the length L is about 212 thousandths of an inch. In some embodiments, a radius of curvature of the rounded region 248 is substantially constant and/or the curvature of the rounded region 248 is substantially monotonic (e.g., progresses only toward, or only approaches, the longitudinal axis $A_L$ in a proximal-to-distal direction). In various embodiments, the length L of the rounded region 248 may be no less than 4, 5, 6, 7, 8, 9, or 10 times an overall length of the needle 204.

Figure 10:
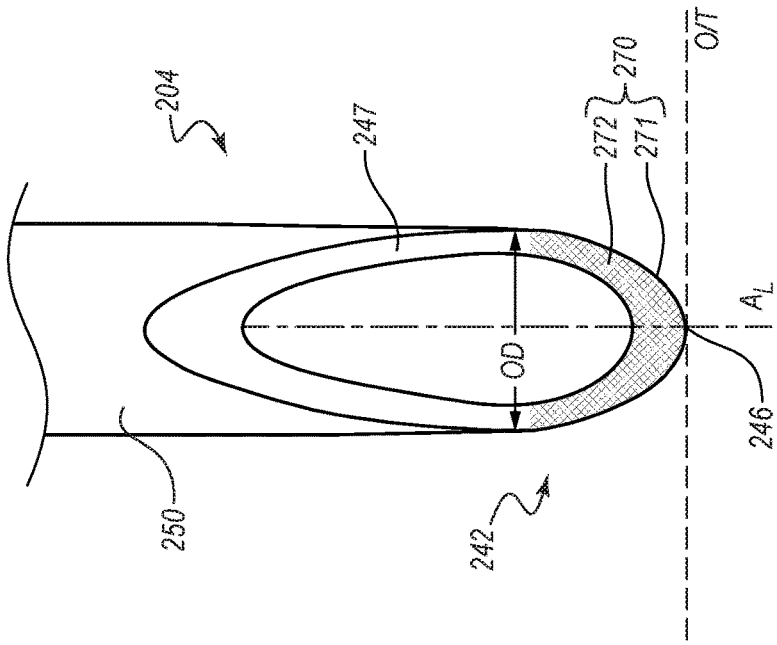
FIG. 10 is an enlarged elevation view of the distal end of the needle.

With reference to FIG. 10, the distal end 242 of the needle 204 can include a cutting end or cutting region 270. The cutting region 270 can include a cutting edge 271 and a cutting face 272. In the illustrated embodiment, the cutting edge 271 is a continuously rounded edge that extends from one lateral side of the needle 204 to an opposite side thereof. Two opposing upper ends of the cutting edge 271 are spaced apart from each other by a distance equal to the outer diameter OD of the shaft 250. Stated otherwise, the cutting edge 271 extends from one side of the OD of the needle 204 to an opposite side of the OD. The cutting face 272 can be a lower portion of the distal face 247 that may contribute to cutting through bone and/or displacing cut bone material. In some instances, the cutting face 272 terminates at a position where an outer diameter thereof corresponds to the OD of the needle 204.

The cutting edge 271 can include the distal tip 246, which may be positioned at the nadir of the cutting edge 271. In the illustrated embodiment, the distal tip 246 is positioned on the cutting edge 271 and on the longitudinal axis $A_L$. The cutting region 270 thus may rotate about the longitudinal axis $A_L$, or about the distal tip 246, during drilling into the bone of a patient. In some instances, the driver 101 (see FIG. 1) may rotate the needle 204 in a single direction, such that only half of the cutting region 270 may cut bone during the insertion event. For example, in the illustrated embodiment, if the needle were to be rotated clockwise, as viewed from above, the portion of the cutting region 270 that is to the right of the longitudinal axis $A_L$ would contribute to cutting, whereas the left portion would not; conversely, if the needle were to be rotated counterclockwise, the opposite would be true. In some instances, the needle 204 may be turned in only one direction during drilling, such as via certain embodiments of the automated driver 108.

In other arrangements, the needle 204 can be rotated back and forth in opposite first and second directions, respectively, and both portions of the cutting region 270 can contribute to cutting the bone. Stated otherwise, the needle 204 can be rotated back and forth, or in opposite directions, and can cut into bone on each stroke. That is, the needle 204 can cut on oppositely directed strokes and, in further embodiments, may do so equally well on each oppositely directed stroke. Stated in yet another manner, the needle 204 can cut bi-directionally. In some instances, such back-and-forth cutting motions may be utilized during manual manipulation of the needle 204, such as when the driver 101 is a manually manipulable handle.

In certain embodiments, such as that illustrated in FIG. 10, the slope of a tangent line at each point along the cutting edge 271 transitions smoothly from one end of the cutting edge 271 to the opposite end thereof. Stated otherwise, the cutting edge 271 can, in some embodiments, be a smooth, rounded surface that is devoid of sharp edges or corners or, stated otherwise, for which the slope of the tangent line is devoid of discontinuities. This may be true generally, or in some embodiments, may only specifically be true locally over a central portion of the cutting edge 271, such as in a region that includes the distal tip 246. For example, rather than coming to a sharp point at the distal tip 246, the cutting edge 271 can be a rounded or smooth curve.

In the illustrated embodiment, the tangent T to the cutting edge 271 at the distal tip 246 is substantially orthogonal to the longitudinal axis $A_L$. Stated otherwise, the tangent T is colinear with an orthogonal line O that both passes through the distal tip 246 and is at a 90-degree angle relative to the longitudinal axis $A_L$. In other embodiments the tangent T at the distal tip 246 defines an angle relative to the orthogonal line O that is no greater than about 10, 15, 30, or 45 degrees.

In some instances, it can be desirable for there to be little or no angle between the tangent T at the distal tip 246 and the orthogonal line O, and further, for the slope of the tangent T to be continuous or to transition smoothly from one side of the distal tip 246 to the other. In certain embodiments, such an arrangement can result in a broad cutting region 270 near the distal tip 246. Stated otherwise, such an arrangement can yield a rounded cutting edge 271 and cutting face 272 that are also close to the orthogonal line O, or stated otherwise, that longitudinally are relatively close (i.e., that are close in the axial direction) to the distal tip 246. The cutting edge 271 and the cutting face 272 thus can more readily cut bone as the needle 204 is rotated about the distal tip 246, as these surfaces at either side of the distal tip 246 are capable of translational movement relative to the bone. In some instances, it is primarily or exclusively the translational movement of the cutting edge 271 and the cutting face 272 relative to the bone surface that scrapes off layers of bone material, or bores through the bone, as the needle 204 is advanced distally. Accordingly, in some instances, it can be desirable for the cutting edge 271 to be broad, or extend outwardly away from the longitudinal axis $A_L$, in the vicinity of the distal tip 246.

In some embodiments, a broad, outwardly extending cutting edge 271 can cut better or more smoothly than a distal tip 246 that is sharply pointed or, stated otherwise, for which a slope of the tangent T is discontinuous and abruptly shifts from a low negative value to a high positive value at the distal tip 246. For example, some sharply pointed distal tips 246 may define an angle that is no greater than 15 or 30 degrees. In some embodiments, the distal tip 246 may come to a point (e.g., the tangent T may be discontinuous thereat, instantly changing from a negative value to a positive value), but an angle defined by that point may be relatively large to facilitate cutting, and may be no less than, for example, about 45, 60, 75, 90, or 105 degrees.

In some embodiments, the cutting edge 271 is symmetrical about the longitudinal axis $A_L$. In some instances, such an arrangement can inhibit wobbling of the needle 204 during drilling.

In some embodiments, such as the illustrated embodiment, only the needle 204 defines any surfaces that cut bone during an insertion event. For example, with reference again to FIG. 11A, in the illustrated embodiment, the obturator 104 is fully recessed relative to the distal face 247 of the needle 204, and thus the obturator 104 does not cut bone when the assembly 109 is rotated for drilling. Accordingly, with reference again to FIG. 10, a physical profile of the cutting edge 271 of only the needle 204 can control or influence the smoothness of a force application profile for a drilling event. For example, in the illustrated embodiment, the physical profile of the cutting edge 271 is smooth and continuous as it transitions from the distal tip 246 (at which the tangent T is substantially horizontal) proximally to the external surface of the shaft 250 (at which the tangent T at either side is substantially vertical). A force profile of a distally directed force substantially along the longitudinal axis $A_L$ may likewise be smooth, or stated otherwise, may be free of abrupt changes.

For example, in some instances, an operator may use the automated driver 108 for an insertion event. The operator may contact the bone with the distal tip 246 of the needle 204 before actuating the automated driver 108. Upon actuation of the driver 108 and rotation of the needle 204, the operator may apply force on the driver 108 that would tend to advance the needle 204 distally through at least an outer surface of the bone. The force applied by the operator may be substantially constant, or may smoothly transition from a high amount to a low amount and/or from a low amount to a high amount throughout the drilling event due to the continuous nature of the cutting edge 271. For example, because there are no discontinuities along the outer surface of the needle 204 (such as may otherwise occur, for example, with a transition from a needle cutting surface to an obturator cutting surface), there may likewise be no discontinuous jumps in the amount of force the operator applies during the drilling event.

With reference again to FIG. 7, the needle tip 246 is formed such that it is positioned in close proximity to the central longitudinal axis $A_L$ of the needle 204. For example, in the illustrated embodiment, the needle tip 246 is positioned directly on the central longitudinal axis $A_L$. In other embodiments, the needle tip 246 may be laterally spaced from the longitudinal axis $A_L$ by a distance that is no greater than 5, 10, 20, or 25 percent of a maximum lateral dimension (e.g., maximum outer diameter) of the needle 204.

In certain embodiments, the distal end 242 of the needle 204 differs from some standard varieties of needles, such as Tuohy, Huber, or other needles with bent tips. Although such needles can include rounded regions and/or one or more beveled edges at their distal ends, similar to those discussed above, their distal tips are generally not in close proximity to the central longitudinal axis. In certain embodiments, the distal end 242 of the needle 204 likewise differs from other standard varieties of needles, such as standard IV needles, including lancet, single-bevel, or other needles with non-bent tips. The distal tips of such needles likewise are generally not in close proximity to the central longitudinal axis. Accordingly, certain needles of this type may wobble against a surface during rotation (e.g., during drilling). Such wobbling can complicate boring through hard bone structures, for example.

Moreover, Huber, Tuohy, and/or other needle varieties with bent tips become non-circular at the tip (e.g., non-circular in transverse cross-section along a longitudinal axis that follows a curvature of a sidewall of the needle) during the forming operation, or otherwise have regions that extend laterally outwardly beyond an outer perimeter defined by a shaft portion of the needle. In some instances, these deformed and/or enlarged regions can result in formation of an access bore that is larger than the shaft of the needle, which may result in the shaft being loosely positioned within the bore.

With reference again to FIG. 10, in some embodiments, the distal face 247 can include a plurality of facets. For example, in some embodiments, lancet grinding may be applied to a bias bevel to yield a lancet point. In certain of such embodiments, the distal face 247 can include three facets, which in some instances, can define three distinct planes. Any other suitable arrangement for the distal face 247 is contemplated.

As previously discussed, however, the illustrated embodiment is particularly well suited for piercing overlaying skin tissue to arrive at the hard bone surface. Additionally, rotation of the illustrated needle 204 causes the cutting surface of the needle to penetrate through the hard bone to the marrow in extremely effective manners. Once access to the marrow has been achieved, the obturator 104 can be removed to allow external communication between an interior of the bone structure and a suitable medical device or system (e.g., fluid line, syringe).

FIG. 11A depicts an early stage of an illustrative method of using the intraosseous access system 100, and is a cross-sectional view of the access assembly 109 in an assembled state. As previously discussed, the access assembly 109 includes the obturator assembly 102, the shield 105, and the needle assembly 202. In some instances, the access assembly 109 will be preassembled, and thus may be removed from any suitable sterile packaging substantially in the configuration depicted in FIG. 11A. In some instances, the cap 107 (see FIG. 1) may first be removed from a distal end of the assembly 102 to arrive at the illustrated configuration.

In the illustrated assembled state, the keyed coupling interfaces 137, 210 of the obturator hub 103 and the needle hub 203, respectively, can cooperate to ensure that a predetermined relationship between the obturator 104 and the needle 204 is achieved. Stated otherwise, the keyed coupling interfaces 137, 210 can ensure that the obturator 104 defines a fixed angular orientation relative to the needle 204. The coupling interfaces 137, 210 may likewise maintain the fixed angular orientation during rotation of the access assembly 109 during an insertion event, e.g., during rotation of the access assembly 109 via the automated driver 108.

In the illustrated embodiment, the distal face 147 of the obturator 104 is slightly recessed relative to the distal face 247 of the needle 204. Additionally, in the illustrated embodiment, the distal faces 147, 247 of the obturator 104 and the needle 204, respectively, are substantially parallel to each other. In some embodiments, the obturator 104 does not cut either through skin or bone during an insertion event. In other embodiments, the distal faces 147, 247 may be substantially flush with each other. The obturator 104 can substantially fill or otherwise block passage into the lumen 251 of the needle 204. For example, in the illustrated embodiment, the distal face 147 of the obturator 104 is substantially the same size as an opening into a distal end of the lumen 251. In various embodiments, an area of the distal face 147 of the obturator 104 is no greater than 5, 10, 15, or 20 percent smaller than an area defined by an inner edge of the distal face 247 of the needle 204. The obturator 104 can inhibit or prevent tissue and/or bone material from entering and/or progressing into the lumen 251 of the needle 204.

The interior surface 253 of the needle 204 and an exterior surface of the obturator 120 can be complementarily shaped and/or otherwise configured to prevent or inhibit ingress of tissue, bone, and/or other matter. In further embodiments, a fit between the obturator 120 and the needle 204 can permit the obturator 120 to be readily removed from needle 204. For example, a snug fit, a loose fit, or a minimal gap may be provided between at least a portion between the obturator 120 and the needle 204.

With continued reference to FIG. 11A, during assembly of the access assembly 109, the arms or projections 132 of the obturator hub 103 can be advanced over the skirt 228 of the needle hub 203. The snap interface or inward protrusions 134 of the projections 132 can grip an underside of the skirt 228 to maintain the obturator hub 103 and the needle hub 203 in a coupled state. In the illustrated embodiment, the skirt 228 is shaped substantially as an outward protrusion, and the inner surface of the arm 132 substantially defines a recess into which the protrusion is received. In other embodiments, the protrusion/recess interface may be reversed. For example, the arm 132 may define a protrusion is received into a recess defined by the skirt 228 to couple the obturator hub 103 with the needle hub 203.

The projection 132 and the skirt 228 may collectively be referred to as a releasable engagement mechanism 262. The releasable engagement mechanism 262 may be configured to keep the obturator hub 103 and the needle hub 203 coupled together during general manipulation of the access assembly 109, such as during removal from packaging and/or coupling thereof with the automated driver 108. The releasable engagement mechanism 262 may, however, provide a relatively weak coupling that is capable of being released upon application of sufficient removal force to the obturator hub 103 in a proximal direction, relative to the needle hub 203. For example, the releasable engagement mechanism 262 may provide a coupling force that tends to keep the obturator hub 103 engaged with the needle hub 203. When a proximally directed force on the obturator hub 103 exceeds the coupling force of the releasable engagement mechanism 262, the releasable engagement mechanism 262 can disengage and permit the obturator hub 103 to be withdrawn from the needle hub 203. In various embodiments, the coupling force (i.e., the force that counteracts a proximally directed force on the obturator hub 103) can be no greater than about 0.25, 0.5, 0.75, 1.0, 1.5, or 2.0 pounds.

In certain embodiments, the releasable engagement mechanism 262 provides a coupling force that is significantly lower than an embedding force between the needle 204 and a bone within which the needle 204 is inserted. Stated otherwise, the releasable engagement mechanism 262 can be configured to permit the obturator hub 103 to be decoupled from the needle hub 203, after the needle hub 203 has been introduced into the bone, by imparting a proximally directed force on the obturator hub 103 that is smaller in magnitude than a force imparted on the cannula 204 by the bone that maintains the cannula 204 positioned in the bone.

Accordingly, in some embodiments, after introducing the access assembly 109 into the bone, a user may simply pull back, or proximally, on the obturator hub 103 with any amount of force that exceeds the coupling force of the releasable engagement mechanism 262, and the obturator hub 103 will automatically disengage from the needle hub 203. Further, the obturator hub 103 can be withdrawn from the needle hub 203 and the patient, and the needle 204 can remain in the bone. In some instances, the user can remove the obturator hub 103 from the needle hub 203 using a single hand after the access assembly 109 has been introduced into the bone. Other suitable arrangements of the releasable engagement mechanism 262 are contemplated.

With continued reference to FIG. 11A, when the access assembly 109 is in the assembled state, the shield 105 can be coupled with each of the obturator 104 and the needle hub 204 in an unlocked state, in which the arms 162, 163 are deflected outwardly away from the longitudinal axis $A_{L-SYS}$. In particular, the proximal end 140 of the obturator 104, which can define a larger diameter than does the recess 150, can extend through an entirety of the shield 105. Stated otherwise, the proximal end 140 of the obturator 104 extends through the lateral extensions 172, 173 and the collar 160. As further discussed below, this larger diameter region of the obturator 104 can maintain the shield 105 in the unlocked state to permit the obturator 104 to translate relative to the shield 105 in a proximal direction when the user desires to remove the obturator hub 103 from the needle hub 204.

When the shield 105 is in the unlocked state, the arms are deflected outwardly, which can seat or otherwise position the outward protrusions 178, 179 of the arms 162, 163 respectively within the groove 227 of the needle hub 203. The outward protrusions 178, 179 thus can cooperate with the groove 227 to maintain the shield 105 in a fixed longitudinal position relative to the needle hub 203 during the initial stages of withdrawal of the obturator 104 through the shield 105. In other embodiments, the groove 227 and the outward protrusions 178, 179 can be reversed. For example, in some embodiments, an inner surface of the needle hub 203 may define one or more inward protrusions, and the arms 162, 163 may define inward recesses into which the inward protrusions are received when the shield 105 is in the unlocked state (relative to the obturator 104) and in the coupled state relative to the needle hub 203. The arms 181, 182 (not visible in FIG. 11A, see FIG. 4) may likewise be maintained in an outwardly deflected state in the configuration depicted in FIG. 11A.

With continued reference to FIG. 11A, when in the assembled state, which may also be referred to as a pre-use or drilling state, the shield 105 defines a low-profile configuration that is relatively close to the longitudinal axis $A_{L-SYS}$ of the access assembly 109. The longitudinal axis $A_{L-SYS}$ may also be referred to as a central axis or as an axis of rotation. That is, during insertion of a distal end of the access assembly 109 into the bone of a patient, the access assembly 109 can be rotated about the axis $A_{L-SYS}$. In many instances, the rotation can be very rapid, such as when the access assembly 109 is coupled with the automated driver 108. In some instances, by defining a low-profile configuration that is close to the rotational axis, the shield 105 can have a low rotational moment of inertia that permits the shield 105 to spin up to speed rapidly and/or permits the shield 105 to stop spinning rapidly once the access assembly 109 in inserted into the bone. The shield 105 may also be relatively lightweight, which can also contribute to a relatively low rotational moment of inertia.

Figure 11C:
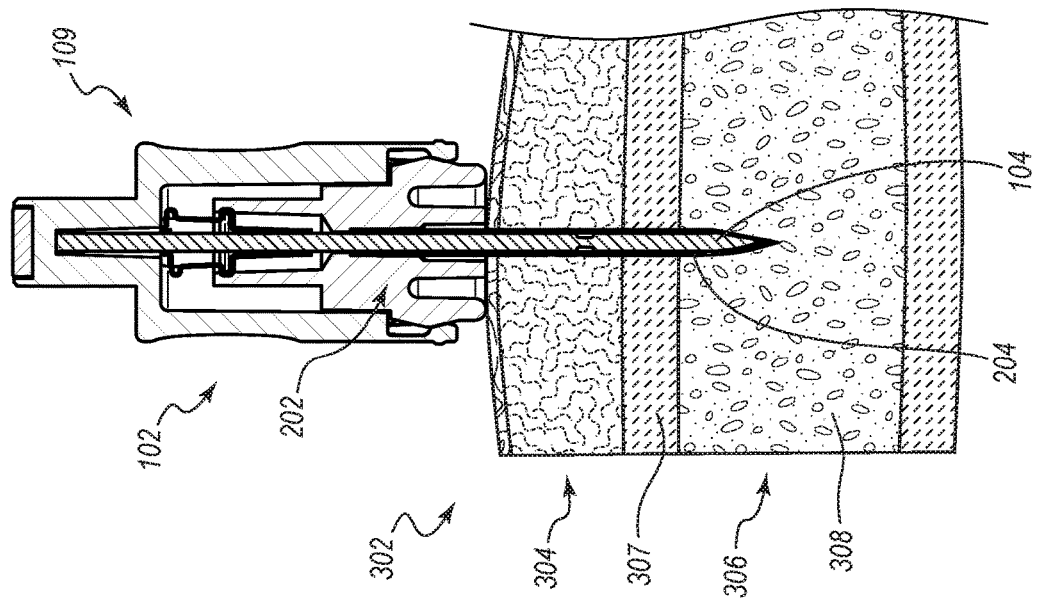
FIG. 11C depicts another stage of the illustrative method and is a cross-sectional view of the access assembly after it has been used to provide access to an interior of the bone of the patient.
Figure 11B:
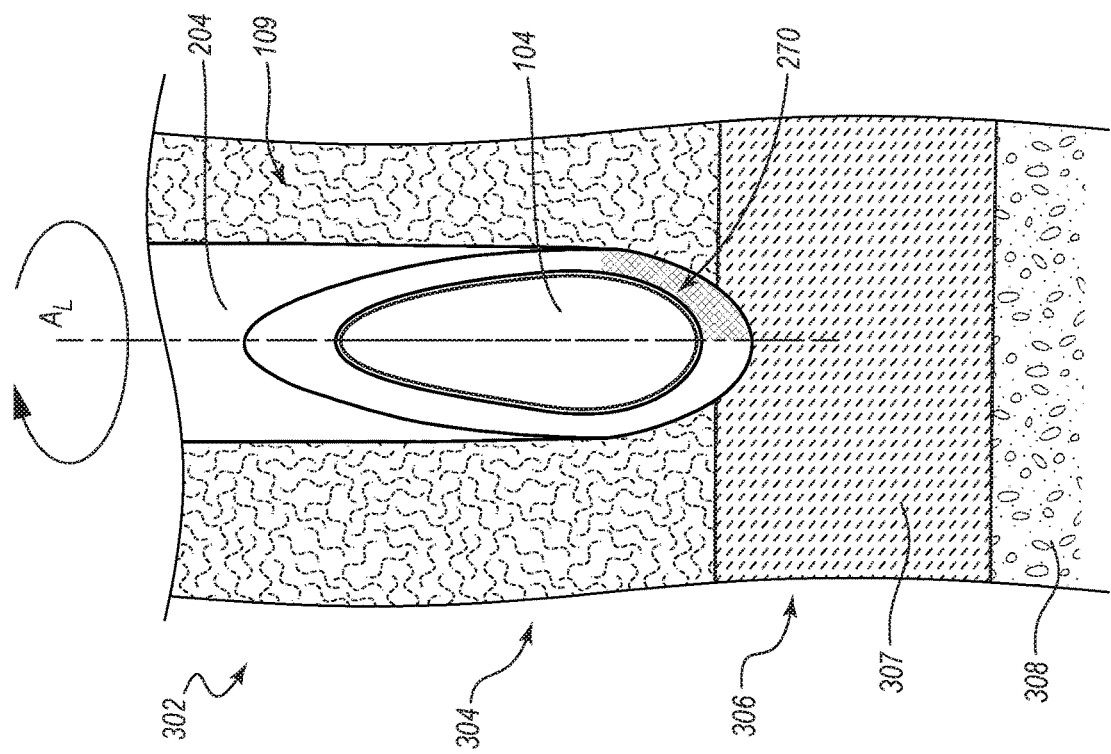
FIG. 11B depicts another stage of the illustrative method and is a plan view of a distal end of an access assembly during drilling thereof into a bone of a patient.

FIG. 11B depicts another stage of the illustrative method of using the intraosseous access system 100. Prior to the illustrated stage, the access assembly 109 can be coupled with a driver 101, such as the automated driver 108. The access assembly 109—or more particularly, the distal ends of the needle 204 and the obturator 104, in the coupled state—are advanced distally through the skin 304 of a patient 302 until the distal tip 246 of the needle 204 contacts an outer surface of a bone 306. As previously discussed, the needle 204 can be particularly well suited to slice through the skin 304. In some instances, the access assembly 109 is advanced distally toward the bone 306 substantially without rotation. The distal end of the needle 204 thus may slice through and separate skin tissue as it proceeds into contact with the bone 306. Upon contact with the bone.

Upon making contact with the bone 306, the operator may actuate the automated driver 108 to rapidly rotate the access assembly 109. In the illustrated embodiment, the access assembly 109 is rotated only in the clockwise direction, as viewed from above. Accordingly, only the highlighted portion of the cutting region 270 may contribute to cutting of the bone 306. The operator applies distally directed force on the automated driver 108, and hence on the access assembly 109, to advance the access assembly 109 through a hard layer 307 of the bone 306 and into the underlying marrow 308. In other methods, the access assembly 109 may instead be rotated through both the skin 304 and then through the hard bone 307. In either case, the operator may sense from tactile feedback once the access assembly 109 has advanced to an interior of the bone 306, due to a sudden decrease in resistance to the drilling. The operator may then cease actuation of the automated driver 108, and may decouple the automated driver 108 from the access assembly 109.

FIG. 11C depicts a subsequent stage of the illustrative method, and shows a cross-sectional view of the access assembly 109 after it has been used to provide access to the interior of the bone 306. After the stage depicted in FIG. 11C, the obturator assembly 102 can be removed from the needle assembly 202. In the illustrated embodiment, the obturator assembly 102 can be removed by pulling it in a proximal direction. Removal of the obturator assembly 102 is described in further detail below with respect to FIGS. 11D and 11E.

Figure 11E:
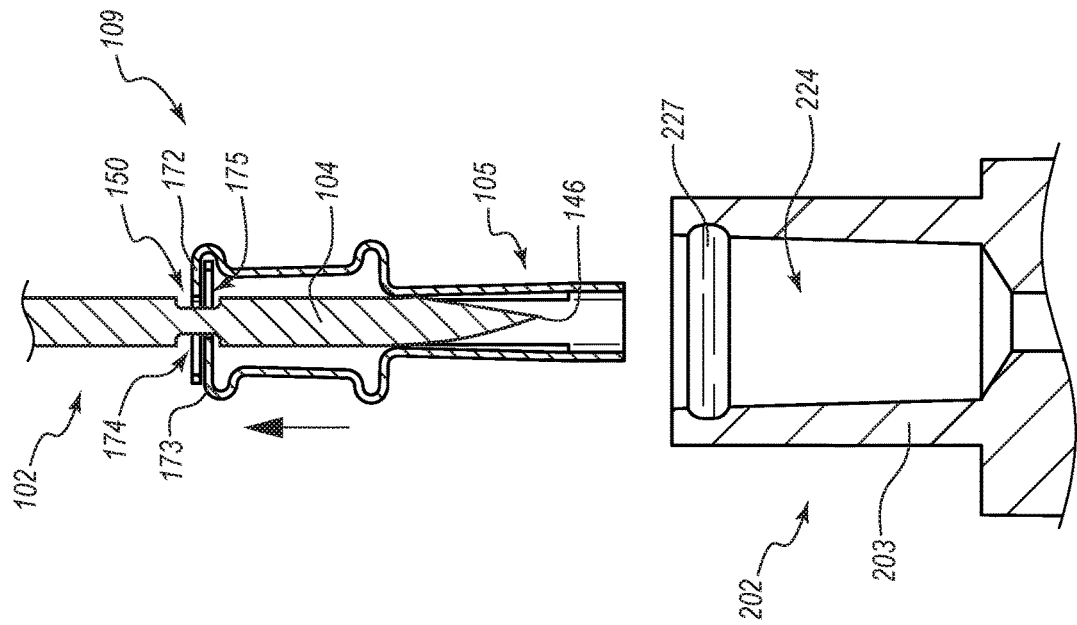
FIG. 11E depicts another stage of the illustrative method and is another enlarged cross-sectional view of the access assembly, wherein the obturator assembly has been fully withdrawn from the needle assembly and the shield is in the locked state relative to the obturator to prevent inadvertent contact with a distal tip of the obturator.
Figure 11D:
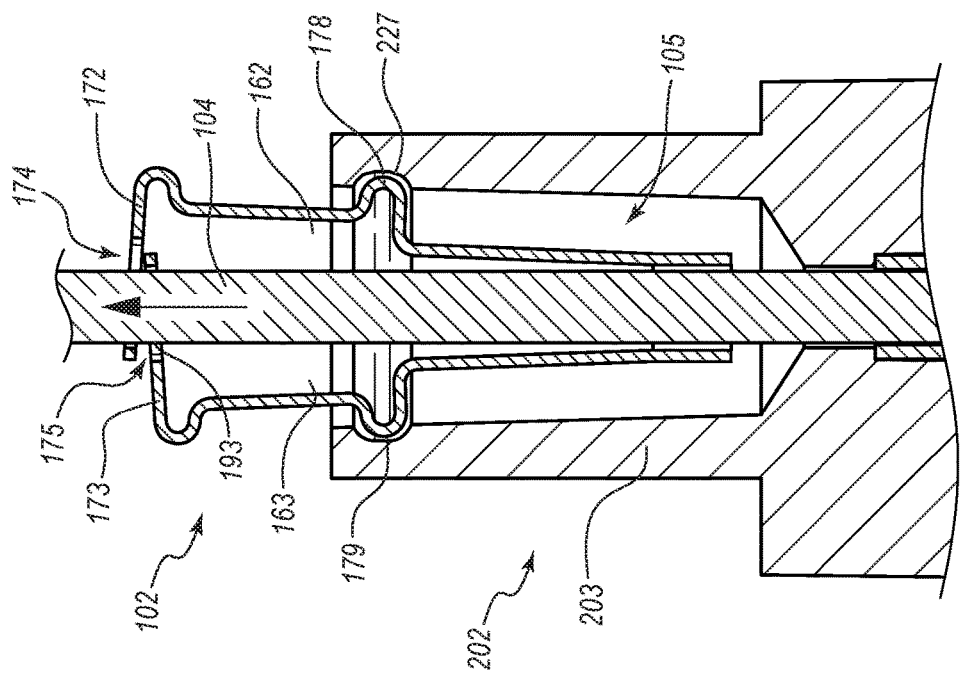
FIG. 11D depicts another stage of the illustrative method and is an enlarged cross-sectional view of a portion of the access assembly, with an obturator hub portion thereof not being shown for purposes of clarity, wherein the obturator assembly is shown being decoupled and withdrawn from the needle assembly while the shield is in an unlocked state relative to an obturator, and is in a coupling state relative to a needle hub.

FIG. 11D is an enlarged cross-sectional view of a portion of the access assembly 109 at a stage of the illustrative method that is subsequent to the stage depicted in FIG. 11C. For purposes of clarity, the obturator hub 103 is not shown, although it would be present in the depicted view, as the obturator hub 103 has only just begun to be withdrawn from the needle hub 203. In particular, in the illustrated stage, the obturator assembly 102 is being decoupled and withdrawn from the needle assembly 202, as depicted by the upwardly directed arrow.

The shield 105 can remain in substantially the same orientation as that depicted in FIGS. 11A and 11C. In particular, the shield 105 can remain in the unlocked state due to the relatively large diameter of the portion of the obturator 104 that is positioned within the openings 174, 175 of the arms 162, 163, respectively. In particular, the obturator 104 can be sufficiently large that portions of the lateral extensions 172, 173 that define the larger, substantially circular portions of the openings 174, 175 (see FIG. 4) translate along the outer surface of the obturator 104. Stated otherwise, the obturator 104 may be sufficiently small to slide or otherwise translate within the larger, substantially circular segments of the openings 174, 175, but may be too large to fit into the constricted, substantially rectangular portions of the openings 174, 175 (see FIG. 4). Accordingly, inner surfaces of the lateral extensions 172, 173 that define the openings 174, 175 can press against the outer surface of the obturator 104 to maintain the arms 162, 163 in the outwardly deflected or displaced state. This outward deflection secures the outward protrusions 178, 179 within the groove 227 of the needle hub 203. The shield 105 thus remains coupled to the needle hub 203.

The shield 105 can remain in the unlocked state as the obturator 104 continues to be withdrawn proximally due to the relatively large diameter of the obturator 104, which may be substantially constant along the full proximal length of the obturator 104. The obturator 104 can continue to maintain the arms 162, 163 in the outwardly deflected or displaced state. This outward deflection secures the outward protrusions 178, 179 within the groove 227 of the needle hub 203. The shield 105 thus remains coupled to the needle hub 203

FIG. 11E is another enlarged cross-sectional view of the access assembly 109 at a subsequent stage of the illustrative method in which the obturator 104 has been fully withdrawn from the needle hub 203. Stated otherwise, the obturator assembly 102 has been fully withdrawn from the needle assembly 202 and continues to be moved away from the needle assembly 202, as depicted by the upwardly directed arrow. Prior to the depicted stage, the obturator 104 is withdrawn proximally by a sufficient amount to bring the recess 150 into the vicinity of the openings 174, 175. Due to the reduced diameter of the recess 150, the constricted portions of the openings 174, 175 fit into the recess 150 and the arms 162, 163 are thus permitted to automatically transition to their unbiased, non-deflected, or non-deformed state (or in other embodiments, this may be a less biased, less-deflected, or less-deformed state). Stated otherwise, the arms 162, 163 can resiliently return to a less bent or unbent state to automatically lock the shield 105 to the obturator 104.

When the shield 105 is in the locked state, portions of the lateral extensions 172, 173 that define the constricted portions of the openings 174, 175 enter into the recess 150 to secure the shield 105 to the obturator 104. Similarly, in the illustrated embodiment, ends of the arms 181, 182 (see FIG. 4) that have previously been deflected outwardly by the larger stem of the obturator 104 can deflect inwardly into the recess 150 as well. When the shield 105 is locked to the obturator 104, movement of the shield 105 relative to the obturator 104 can be prevented or delimited in one or more directions (e.g., longitudinally and/or rotationally). In some embodiments, interference between the lateral extensions 172, 173 and proximal and distal faces of the recess 150, respectively, can delimit longitudinal movement of the shield 105 relative to the obturator 104. In further instances, the ends of the arms 181, 182 (see FIG. 4) that are also present with the recess 150 can serve as a backup safety measure, and may engage with a proximal face of the recess 150 to maintain engagement between the shield 105 and the obturator 104 if sufficient force is applied to the shield 105 in a proximal direction, relative to the obturator, to dislodge the lateral extensions 172, 173 from the recess 150. Upon dislodgement of the lateral extension 172, 173 from the recess 150, and upon slight additional proximal movement of the shield 105, the proximal ends of the arms 181, 182 engage the proximal face of the recess 150 to prevent any further proximal movement of the shield 105 relative to the obturator 104.

In the illustrated embodiment, when the arms 162, 163 automatically transition to the locked state relative to the obturator 104, the arms 162, 163 substantially simultaneously decouple the shield from the needle hub 203. In particular, in the illustrated embodiment, the inward movement of the arms 162, 163 causes the outward protrusions 162, 163 to exit the groove 227 of the needle hub 203. This frees the shield 105 to move relative to the needle hub 203, such as for proximal movement in the longitudinal direction to exit the lumen 224. The shield 105 naturally remains in the locked state relative to the obturator 104 and restricts access to the distal tip 146 of the obturator 104.

With reference again to FIG. 4, as previously discussed, the shield 105 can define a cage or enclosure 180 that substantially encompasses the distal tip 146 of the obturator 104 to restrict access to the distal tip 146 when the shield 105 is locked to the obturator 104. In the illustrated embodiment, the collar 160 of the shield 105 defines a fixed opening 167 at a distal end thereof. That is, a shape of the opening 167 does not change when the shield 105 transitions from the unlocked state to the locked state. In a limited sense, the distal tip 166 does not cover the distal tip 146 of the obturator 104, in that the distal tip 146 is viewable through the opening 167. Nevertheless, the shield 105 may still be said to cover the distal tip 146, as the shield 105 is capable of preventing inadvertent contact with the distal tip 146. For example, the opening 167 can be sufficiently small to prevent a practitioner or other individual from inserting any portion of skin through the opening 167 and into contact with the tip 146. In other embodiments, the opening 167 may be smaller and/or may be configured to close when the shield 105 transitions to the locked state. For example, in some embodiments, a cantilevered arm, valve, elastomeric septum, or other naturally closing device may be positioned at the opening 167.

Figure 12B:
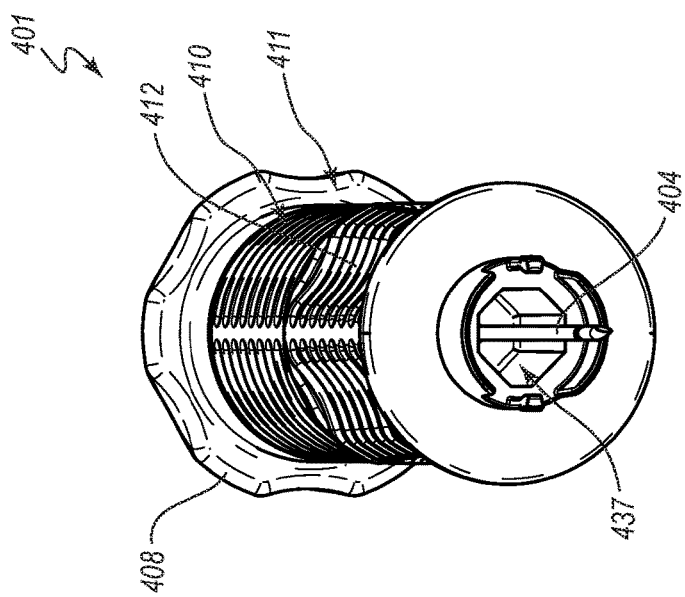
FIG. 12B is a perspective view of the manual driver.
Figure 12A:
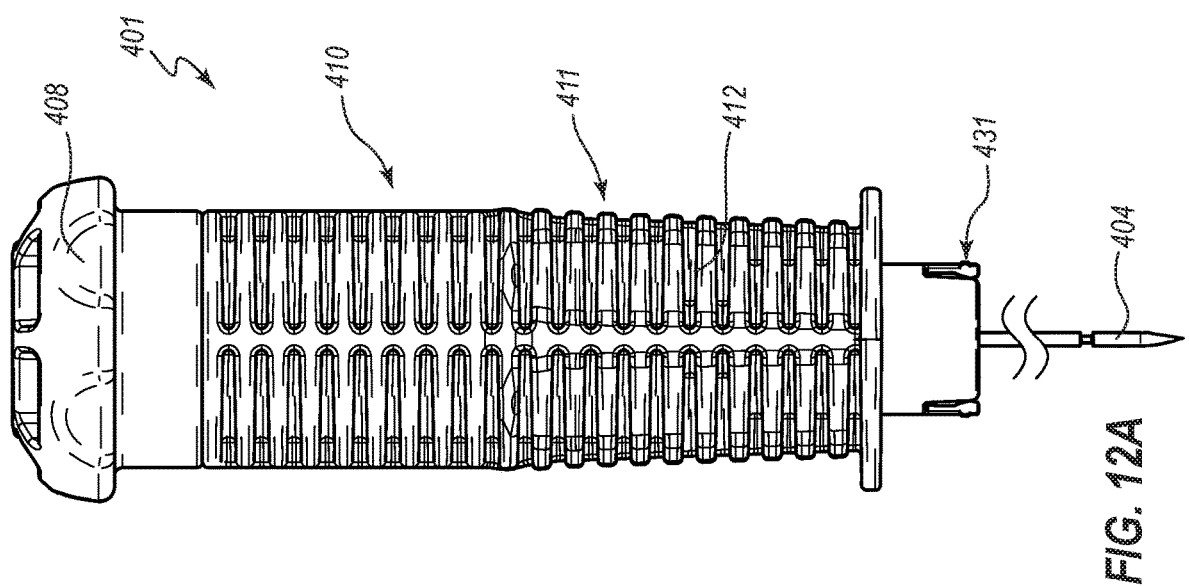
FIG. 12A is an elevation view of an embodiment of a manual driver that is compatible with at least a portion of the intraosseous access system depicted in FIG. 1.

FIGS. 12A and 12B depict elevation and perspective views, respectively, of another embodiment of a driver 401. In the illustrated embodiment, the driver 401 is a manual driver 408 that can be used in place of the automated driver 108 and, further, incorporates various components of the obturator assembly 102. In other embodiments, the manual driver 408 may instead merely replace the automated driver 108—for example, a distal portion of the manual driver 408 may include a connection interface, similar to that of the connection interface 112 of the automated driver 108, via which the manual driver 408 can connect directly to the obturator assembly 102. In the illustrated embodiment, the manual driver 408 is configured to be coupled with the needle assembly 202 and can be manipulated by one or more hands of a practitioner to introduce the needle 204 into the bone of a patient.

The manual driver 408 includes a handle 410 that can be elongated in a longitudinal direction. The handle 410 can include any suitable gripping features 411, such as a plurality of horizontal grooves 412 that may enhance a grip of the user on the handle 410. An outer contour of the handle 410 may have any suitable ergonomic configuration.

The manual driver 408 can include a pair of coupling members 431 and a coupling interface 437 that resemble the like-numbered coupling members 131 and coupling interface 137 described above. These features may function in like manners to couple the manual driver 408 to the needle assembly 202. Similarly, the manual driver 408 can include an obturator 404, such as the obturator 104.

The manual driver 408 can be coupled to the needle assembly 202, and may be used to provide intraosseous access. The illustrated embodiment can cut bone when rotated in either direction about the longitudinal axis. In some instances, a practitioner can press downwardly against a proximal end of the handle 410 and can rotate the handle 410 back and forth to insert the needle into the bone.

Figure 13:
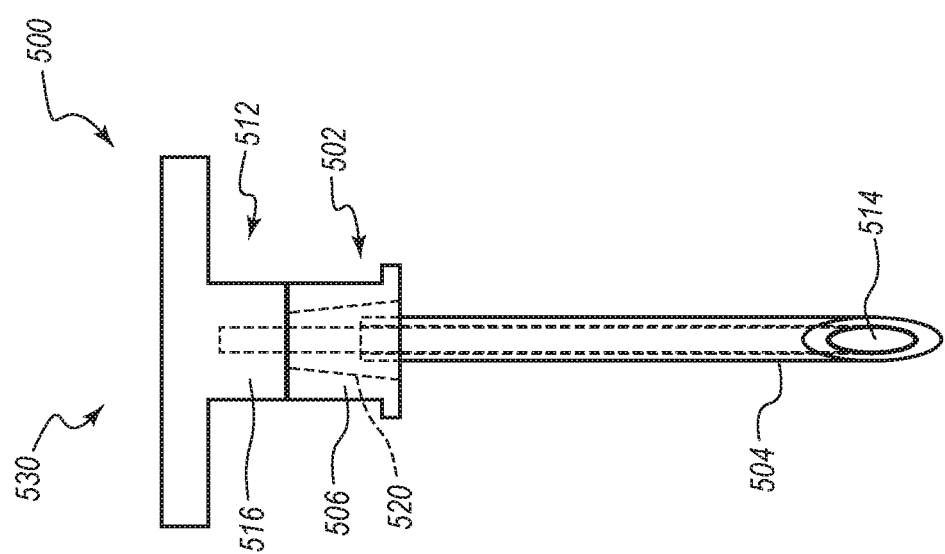
FIG. 13 is an elevation view of another embodiment of an intraosseous access system that includes another embodiment of a manual driver.

FIG. 13 schematically depicts another embodiment of an intraosseous access system 500 that resembles the system 100 in many respects. The system 500 includes a needle assembly 502 having a needle 504 that is fixedly secured to a connector 506. The system 500 further includes an obturator assembly 512 that includes an obturator 514 fixedly secured to a connector 516. The assemblies 502, 512 are depicted in a coupled state. The assemblies 502, 512 are coupled via a connection interface 520. The connector 516 defines a T-shaped grip 530 or handle that can be used to manually manipulate the system 500 to gain intraosseous access.

The connection interface 520 can be of any suitable variety. As further discussed below, in some embodiments, the connection interface 520 may further be used to connect the needle 504 to any suitable medical interface after the obturator assembly 512 has been removed. For example, the interface 520 may be configured as a Luer fitting, which may be coupled with external tubing (e.g., an IV line), aspiration equipment, and/or other medical devices after the obturator assembly 512 has been removed. In other embodiments, the connection interface 520 may be used for connection to the obturator assembly 512 and an additional or separate connection interface may be used for connection (e.g., subsequent connection) to one or more medical devices that utilize the intraosseous access provided by the needle assembly 502. In still other embodiments, the connection interface 520 may be used for connection to the one or more medical devices, whereas the additional connection interface is used for connection to the obturator assembly 512.

The connector 516 is fixedly secured to a proximal end of the obturator 514. The connector 516 can be configured to selectively couple with the connector 506 of the needle assembly 502, as previously described. For example, in some embodiments, the connection interface 520 of the connector 506 can comprise a Luer fitting, and the connector 516 of the obturator assembly 512 can comprise a complementary Luer fitting (not shown) configured to couple therewith. Any suitable connection interface for coupling the connectors 506, 516 is contemplated.

In the illustrated embodiment, when the needle assembly 502 and the obturator assembly 512 are in a coupled state, the obturator 514 extends through the connector 506 and through a lumen of the needle 504. In certain embodiments, once intraosseous access has been established, the needle assembly 502 may remain in the bone, whereas the connector 516 can be decoupled from the connector 506, and the obturator assembly 512 can be removed from the needle assembly 502. Any suitable configuration for the connector 516 that permits manual application of sufficient translation and/or rotational forces to the coupled assemblies 502, 512 to penetrate hard bone tissue is contemplated.

Figure 14:
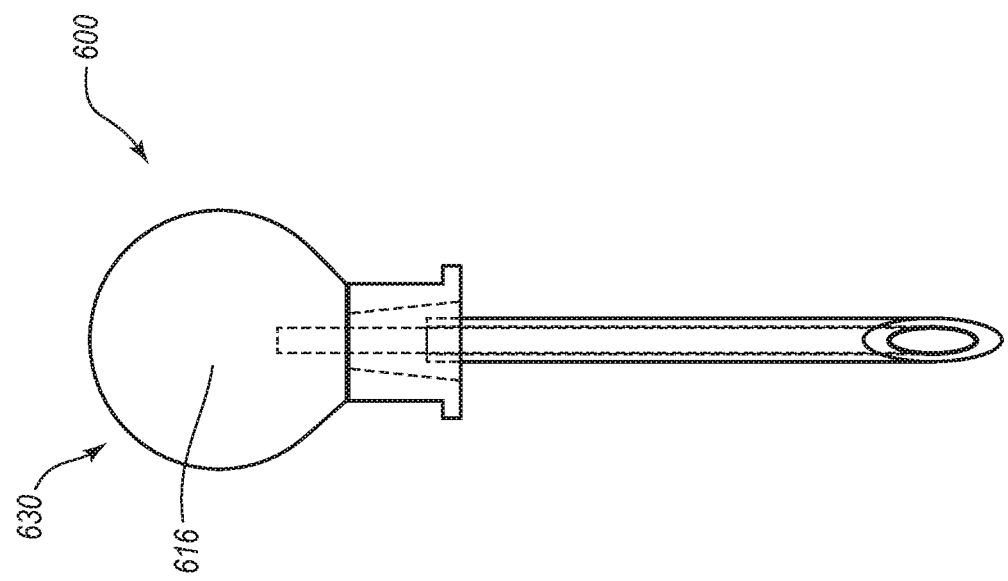
FIG. 14 is an elevation view of yet another embodiment of an intraosseous access system that includes yet another embodiment of a manual driver.

FIG. 14 depicts another embodiment of an intraosseous access system 600 that can resemble the intraosseous access systems described above in certain respects. The system 600 can be identical to the system 500, except that a connector 616 thereof can be formed as a manual awl handle 630 that can be used to manually manipulate the system 600 to gain intraosseous access, rather than a T-shaped configuration. Any suitable configuration of the connector 616 is contemplated.

Any suitable method may be employed to form needles such as those described above. By extension, such methods may form a subset of the processes used to manufacture any of the access assemblies and/or intraosseous access systems described herein. In some embodiments, a needle is formed from a cylindrical tube. The tube is bent in such a way as to maintain a circular transverse perimeter, or cross-section, along a full central axis thereof, where the central axis follows the bend of the tube in manners such as previously discussed. A distal face (e.g., the distal face 247) of the distal tip can be formed by any suitable technique, such as grinding.

In other or further embodiments, the formation process ensures that the distal end (e.g., the distal end 242) of the needle has one or more of the properties previously discussed, such as a lateral cross-section that does not extend transversely outwardly beyond a lateral cross-section or perimeter defined by the shaft portion that extends proximally from the distal end of the needle. For example, in some embodiments, the outer surface of the tube from which the needle is formed is constrained in at least the region at which bending is performed during manufacturing. The constraint may be provided by any suitable assembly structure, such as a fixture (see, e.g., the fixture 800 depicted in FIG. 16).

In some methods, the fixture is used to bend a tube from which the needle is formed prior to grinding, and then the tip of the needle is ground in a subsequent step. In other methods, the fixture is used after the tip of the needle has been formed via grinding. In various embodiments, the distal end of the needle is formed such that a diameter of the hole or bore formed by the distal end of the needle during an access event is equal to or smaller than the outside diameter of the shaft. Stated otherwise, a perimeter of the hole or bore formed by the distal end of the needle can be equal to or smaller than the transverse perimeter of the shaft.

FIGS. 15A-15E depict various steps in an illustrative method of forming a needle, such as the needle 204 discussed above. By extension, the illustrative method may form a subset of the processes used to manufacture, for example, the access assembly 109.

Figure 15A:
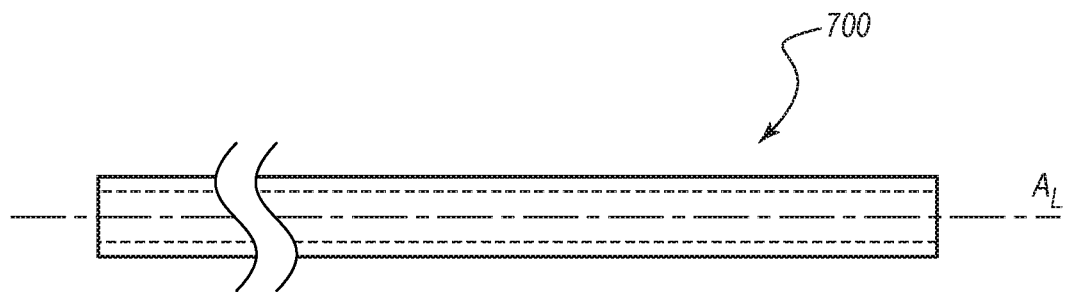
FIG. 15A depicts a stage of an illustrative method of forming a needle, which may more generally be part of an illustrative method of forming an interosseous access system, and is an elevation view of an embodiment of a tube that has been straightened.

With reference to FIG. 15A, in an early stage of the process, a stock supply of tubing is cut to length to yield a tube 700. In some instances, the stock tubing is initially wound so as to have a curvature. Accordingly, in some embodiments, the tube 700 is straightened, whether before or after being cut to length. The tube 700 can be substantially cylindrical after straightening. Stated otherwise, each of an interior surface and an exterior surface of the tube 700 can be substantially cylindrical. The tube 700 can define a longitudinal axis $A_L$, and a transverse cross-sectional perimeter of the tube 700 can be substantially circular.

Figure 15B:
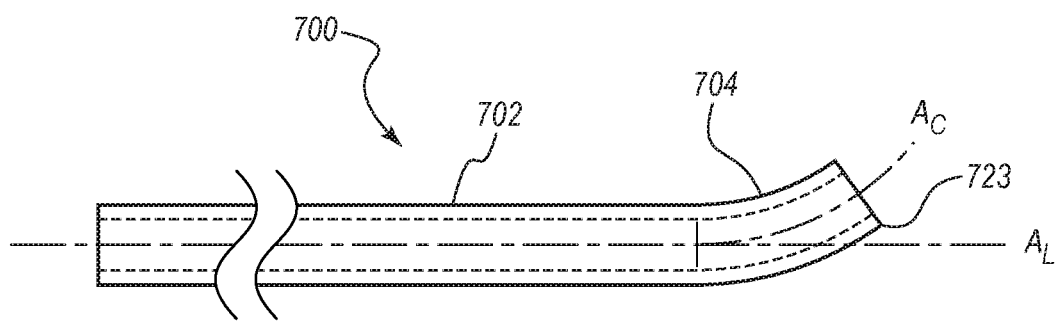
FIG. 15B depicts another stage of the illustrative method in which a distal end of the tube has been bent.

With reference to FIG. 15B, in another stage of the process, a distal end of the tube 700 can be bent by a desired amount. Bending the tube 700 can yield a shaft 702, which can remain substantially cylindrical, and a bent region 704 that extends distally from the shaft 702. The bent region 704 can be formed by a sufficient deflection of the tube 700 such that the bent region 704 of the tube intersects the longitudinal axis $A_L$.

Figure 15C:
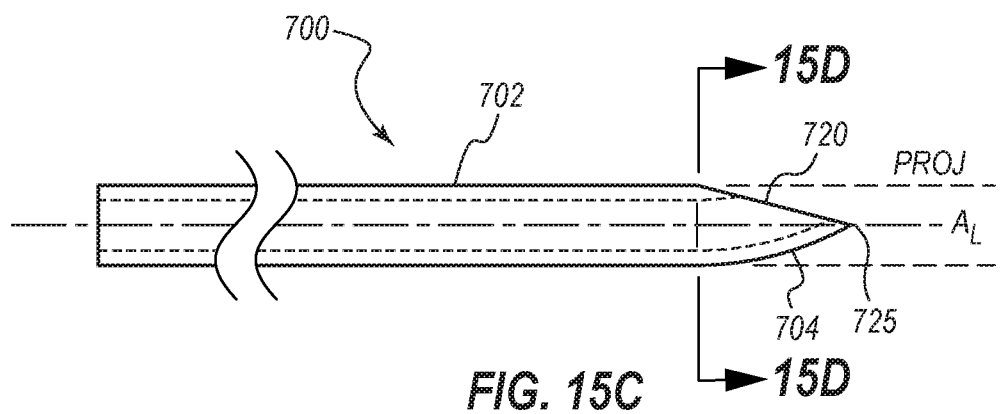
FIG. 15C depicts another stage of the illustrative method in which a simple bias grind has been applied to the distal end of the tube.

With reference to FIG. 15C, in another stage of the process, a portion of the bent region 704 can be ground or otherwise removed to form a distal face 720. The distal face 720 can correspond to the distal face 247 of the needle 204 discussed above. In some instances, the distal face 720 can be formed as a simple bias grind. Grinding the distal end of the tube 700 can yield a distalmost point 725 of the tube. For example, prior to bending (FIG. 15A), a distal tip of the tube 700 can terminate at a face, such as a planar annulus. After bending (FIG. 15B), the distalmost portion of the tube 700 can instead terminate at a distalmost point 723. However, at that stage, the distalmost point 723 is not directly on the longitudinal axis $A_L$. After grinding (FIG. 15C), the tube 700 can terminate at a different distalmost point 725 that is now on the longitudinal axis $A_L$.

Figure 15D:
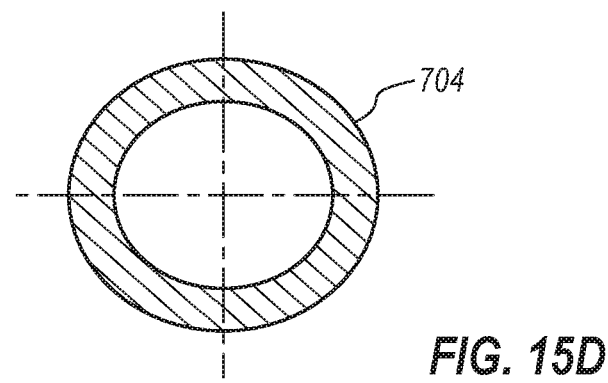
FIG. 15D is a cross-sectional view of the tube, taken along the view line 15D-15D in FIG. 15C, that depicts an ovalized profile of the tube in a region of the tube that has been bent.

With reference to FIG. 15D, bending of the tube 700 can cause at least a portion of the bent region 704 to define a substantially ovalized profile. The profile can be a cross-section tube 700 along a plane that is orthogonal to a central axis $A_C$ through the tube 700. In FIG. 15C, the central axis $A_C$ is aligned with the longitudinal axis $A_L$ throughout the shaft 702, and also at the cross-sectional plane of FIG. 15D. In some instances, the central axis $A_C$ can be curved so as to be centered within the bent region 704, as shown in FIG. 15B.

With continued reference to FIG. 15D, the ovalized profile can be elongated in a first dimension that is substantially orthogonal to the central axis $A_C$. In the illustrated configuration, the first dimension is the horizontal dimension.

Figure 15E:
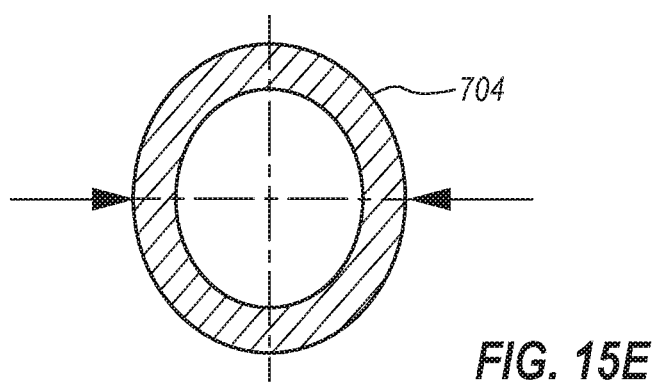
FIG. 15E is a cross-sectional view of the tube such as that shown in FIG. 15D that depicts another stage of the illustrative method in which compressive forces are applied to the tube along an axis of elongation (e.g., along a major axis of the ovalized profile of the tube) and toward a longitudinal axis of the tube.

With reference to FIG. 15E, in another stage of the illustrative method, a compressive force, or compressive forces, may be applied to the bent region 704 of the tube 704 along the first dimension, thus urging the bent region 704 inwardly toward the central axis $A_C$. The compressive forces are schematically depicted as inwardly directed arrows. Any suitable instruments or machinery may be used to apply the forced. For example, in some embodiments, the forces may be applied by a vice or other device. The vice may be marked such that the vice is tightened to a predetermined width to render at least a portion of the bent region 704 circular (as in FIG. 15F). In some instances, the compressive forces are applied to the bent region 704 so as to narrow the cross-sectional profile of the bent region 704 along the first dimension, while elongating the bent region 704 along a second dimension that is orthogonal to both the first dimension and the central axis $A_C$. In the illustrated embodiment, the bent region 704 is elongated in the vertical dimension, and narrowed in the horizontal dimension.

Figure 15F:
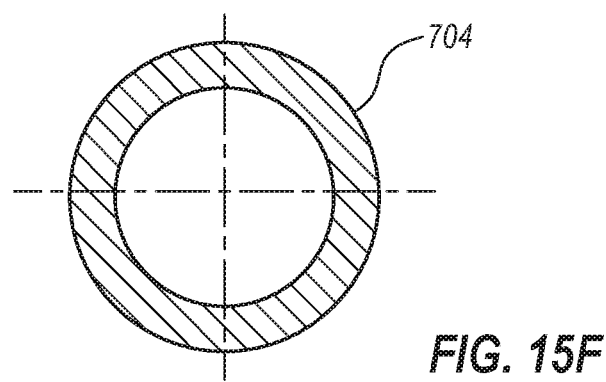
FIG. 15F is a cross-sectional view of the tube such as that shown in FIG. 15D that depicts another stage of the illustrative method in which the compressive force has been removed from the tube, thus allowing the tube to move naturally outwardly, or to rebound, into a more circularized configuration.

With reference to FIG. 15F, in another stage of the illustrative method, the compressive forces can be removed or from the bent region 704. Stated otherwise, in some instances, the bent region 704 may be released. In some instances, releasing the bent region 704 can permit the bent region 704 to naturally rebound to a less ovalized orientation, which may be substantially circular, in some instances. After removal of the compressive forces, an entirety of the bent region 704 may be circumscribed by, enveloped by, or otherwise fit within an imaginary projection PROJ (FIG. 15C) of the outer cylindrical surface of the shaft 702. The imaginary projection PROJ may be thought of as the original position of the bent region 704, prior to bending, or may be thought of as a continuation of the cylindrical surface that remains centered along the longitudinal axis $A_L$. Stated in another way, after compression has been applied, no portion of the distal region 704 extends transversely outwardly beyond the imaginary projection of the outer cylindrical surface of the shaft 702.

Various stages of the illustrative method just described may be performed in different order and/or may be performed simultaneously with other stages. For example, in some instances, the bending stage may be performed simultaneously with the compressive stage. In some instances, grinding may take place prior to bending. Other alterations of the illustrative method are contemplated.

Some methods of forming an obturator, such as the obturator 104 discussed above, can be the same or substantially the same as the illustrative methods discussed with respect to formation of the needle 204. Rather than using a tube, however, the methods can use a rod or wire.

Figure 16:
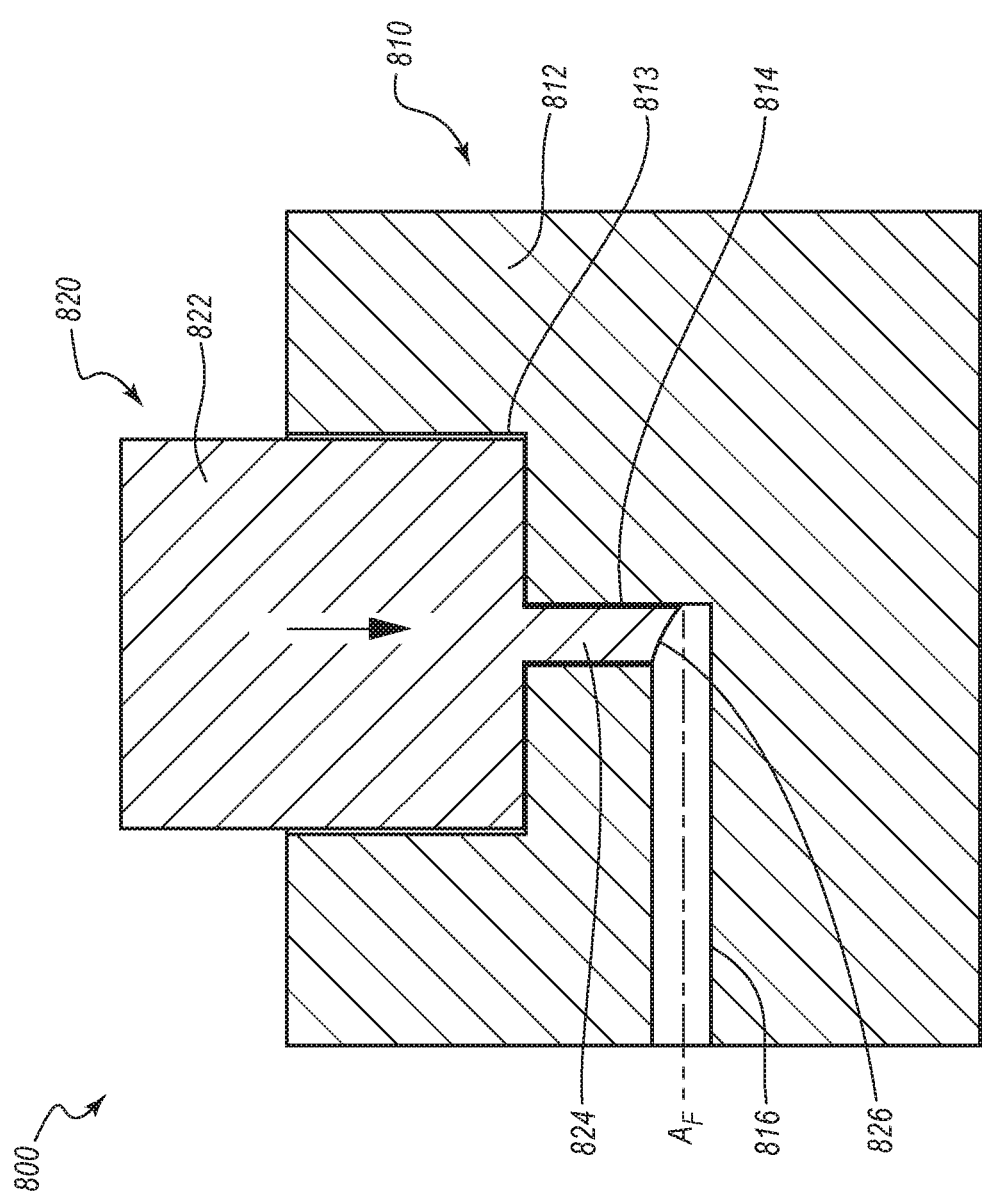
FIG. 16 is a cross-sectional view of an embodiment of a fixture that may be used in certain methods of forming or shaping a distal end of a needle compatible with various intraosseous access systems described herein.

FIG. 16 is a perspective view of a fixture 800 that can be used to form a distal end of a needle, or an obturator, such that the distal end thereof exhibits one or more of the properties previously described. In the illustrated embodiment, the fixture 800 includes a base 810 and a forming plunger 820. The base 810 includes a body 812 that has a plunger recess 813, a plunger bore 814, and a needle bore 816 formed therein. The needle bore 816 defines a central longitudinal axis $A_F$. The plunger 820 includes a body 822 and a press 824. A distal end of the press 824 defines a shaping surface 826.

In certain examples of needle-formation procedures, a distal end of a tube (e.g., a tube formed of stainless steel) is ground in any suitable manner. For example, in some methods, an angled tip may be formed via a simple bias grind (e.g., via any known manner for such grinding). In other or further methods, one or more lancet grinds may be applied in forming the tip. The tube may initially terminate at a flat face. Grinding the tube can provide the tube with a distal tip, or stated otherwise, a distal end of the tube may come to a distalmost point.

An outer diameter of the tube can be substantially the same as or only slightly smaller than an inner diameter of the needle bore 816. Accordingly, the tube can be readily inserted into and withdrawn from the needle bore 816. Moreover, the needle bore 816 can constrain the tube during tip formation, thus preventing a distal end of the tube from assuming a shape having a transverse perimeter that is either larger a transverse cross section of a more proximal portion of the tube or that otherwise extends outside of said transverse cross section of the proximal portion of the tube (e.g., has a maximum width that exceeds a diameter of the proximal portion).

In some procedures, the plunger 820 is retracted to ensure a distal end of the needle bore 816 is unobstructed. The plunger 820 may either be retracted within the plunger recess 813 (e.g., partially retracted) or may be retracted completely from the plunger recess 813 (e.g., fully retracted).

The angled tip of the tube is then inserted into the needle bore 816 with the angled surface of the tube facing down (in the illustrated orientation), or stated otherwise, in a direction away from the plunger bore 814. The plunger 820 is then pressed downward as far as possible into the position depicted in FIG. 16. In this end position, the distal-most point of the shaping surface 826 of the plunger 820 is approximately aligned with the central longitudinal axis $A_F$ of the needle bore 816. The central longitudinal axis $A_L$ of the needle (see FIG. 6) thus formed is substantially collinear with the central longitudinal axis $A_F$ of the needle bore 816. Accordingly, after shaping of the distal end of the ground tube, the resultant needle tip is in close proximity to the central longitudinal axis Ax of the needle. The needle can then be removed from the needle bore 816.

The body 812 of the base 810 can be formed of any suitable material. The material can be sufficiently hard to resist deformation and instead maintain its shape and impart the same shape to the distal end of the needle during a tip-shaping procedure.

Certain embodiments disclosed herein can advantageously reduce heating during automated drilling. Other or further embodiments can render drilling procedures smoother and more consistent, which can contribute to safety and/or ease-of-use considerations. For example, in some instances, rather than beginning a drilling procedure by spinning a sharp point against the bone, and then eventually engaging cutting surfaces of the drilling device, a consistent cutting area can be applied, and the amount of that cutting area in use at any given time may increase smoothly up to a maximum value.

The term "patient" is used broadly herein and is not intended to be limiting. A patient can be, for example, any individual who undergoes any of the methods or treatments discussed herein, whether in a hospital, first responder, or other setting. The term "patient" includes humans, mammals, or any other animal possessing anatomy compatible with embodiments described herein.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:
1. An intraosseous access system comprising:
 a needle that defines a lumen and a longitudinal axis about which the needle is configured to be rotated to cut into a bone of a patient, the needle comprising:
  a proximal end configured to remain at an exterior of the patient during use;
  a distal end configured for insertion through the skin of the patient into contact with the bone of the patient; and
  a distal tip at a distalmost point of the distal end of the needle, the distal tip being positioned on the longitudinal axis of the needle;
 an obturator sized to be received within the lumen of the needle and configured to inhibit material from entering the needle as the system is inserted into said bone; and
 a safety shield configured to automatically lock onto a distal end of the obturator when the obturator is removed from the lumen of the needle to prevent inadvertent contact with a distal tip of the obturator.

2. The intraosseous access system of claim 1, wherein the needle further comprises a shaft that extends proximally from the distal end of the needle, the shaft defining a lateral perimeter along a plane that is perpendicular to the longitudinal axis, and wherein no portion of the distal end of the needle is laterally distanced from the longitudinal axis of the needle by an amount exceeding a distance between the lateral perimeter of the shaft and the longitudinal axis.

3. The intraosseous access system of claim 1, wherein the needle further comprises a shaft that extends proximally from the distal end of the needle, the shaft defining a cylindrical outer surface, and wherein no portion of the distal end of the needle extends laterally outwardly beyond a continuation of the cylindrical outer surface that passes over the distal end of the needle.

4. The intraosseous access system of claim 1, wherein:
 the needle comprises an inner wall that defines the lumen;
 the needle further defines an opening at the distal end of the lumen, wherein a plurality of planes are proximal of the opening and contact the inner wall at right angles thereto; and
 a cross-sectional area of the lumen at each plane that is proximal of the opening and that contacts the inner wall at right angles thereto varies by no greater than 50 percent of a maximum cross-sectional area of the lumen.

5. The intraosseous access system of claim 1, wherein:
 the needle comprises an inner wall that defines the lumen;
 the needle further defines an opening at the distal end of the lumen, wherein a plurality of planes are proximal of the opening and contact the inner wall at right angles thereto; and a cross-section of the lumen at each plane that is proximal of the opening and that contacts the inner wall at right angles thereto is substantially circular.

6. The intraosseous access system of claim 1, wherein the distal end of the needle comprises a rounded cutting edge that extends from a first side of the needle to a second side of the needle that is opposite from the first side, and wherein a slope of a tangent to the cutting edge transitions continuously from the first side of the needle to the second side of the needle.

7. The intraosseous access system of claim 1, wherein the distal end of the needle comprises a cutting edge that comprises the distal tip of the needle, and wherein a tangent line to the cutting edge at the distal tip is perpendicular to the longitudinal axis of the needle.

8. The intraosseous access system of claim 1, wherein the needle defines a cutting surface at a distal end thereof and wherein a distal end of the obturator is either flush with or recessed relative to the cutting surface so as not to contribute to any cutting of the bone of the patient when the needle is rotated.

9. The intraosseous access system of claim 1, wherein a cutting surface of the needle comprises a single bias grind.

10. The intraosseous access system of claim 1, wherein the distal end comprises a planar surface that extends proximally from the distalmost point and is at an angle relative to the longitudinal axis.

11. The intraosseous access system of claim 10, wherein the angle is no greater than 15 degrees.

12. The intraosseous access system of claim 10, wherein the distal end further comprises a rounded region that extends away from the planar surface.

13. The intraosseous access system of claim 12, wherein the obturator comprises a rounded region and a planar surface, and wherein the rounded regions and the planar surfaces, respectively, of the obturator and the needle align with each other when the obturator is coupled with the needle.

14. The intraosseous access system of claim 1, wherein the obturator defines a groove configured to receive a portion of the safety shield to prevent or inhibit longitudinal movement of the safety shield relative to the obturator when the safety shield locks onto the obturator.

15. The intraosseous access system of claim 1, wherein the obturator is attached to a connector configured to couple the system with a driving device.

16. The intraosseous access system of claim 15, wherein the needle is attached to an additional connector, and wherein the connectors are configured to selectively attach to and detach from each other.

17. The intraosseous access system of claim 16, wherein the connectors are keyed to ensure that the needle and the obturator maintain a fixed angular orientation relative to each other when the connectors are attached to each other.

18. An intraosseous access system comprising:
   a needle that defines a lumen and a longitudinal axis about which the needle is configured to be rotated to cut into a bone of a patient, the needle comprising:
      a proximal end configured to remain at an exterior of the patient during use;
      a distal end configured for insertion through the skin of the patient into contact with the bone of the patient; and
      a distal tip at a distalmost point of the distal end of the needle, the distal tip being positioned on the longitudinal axis of the needle; and
   an obturator sized to be received within the lumen of the needle and configured to inhibit material from entering the needle as the system is inserted into said bone,
   wherein the obturator is attached to a connector configured to couple the system with a driving device,
   wherein the needle is attached to an additional connector, and wherein the connectors are configured to selectively attach to and detach from each other.

19. The intraosseous access system of claim 18, wherein the connectors are keyed to ensure that the needle and the obturator maintain a fixed angular orientation relative to each other when the connectors are attached to each other.

* * * * *